United States Patent [19]
Ding et al.

[11] Patent Number: 5,869,478
[45] Date of Patent: Feb. 9, 1999

[54] SULFONAMIDO SUBSTITUTED BENZOPYRAN DERIVATIVES

[75] Inventors: Charles Z. Ding, Plainsboro, N.J.; Karnail S. Atwal, Newtown, Pa.

[73] Assignee: Bristol-Myers Squibb Company, Princeton, N.J.

[21] Appl. No.: 481,007

[22] Filed: Jun. 7, 1995

[51] Int. Cl.$^6$ .......................... A61K 31/35; C07D 311/68
[52] U.S. Cl. .................. 514/212; 514/228.2; 514/233.5; 514/253; 514/320; 514/324; 514/422; 514/456; 540/596; 544/58.2; 544/62; 544/151; 544/326; 546/196; 546/202; 548/524; 549/404
[58] Field of Search .................................. 546/196, 202; 514/320, 324, 212, 233.5, 228.2, 253, 456; 548/525; 540/596; 544/151, 58.2, 62, 376; 549/404

[56] References Cited

U.S. PATENT DOCUMENTS

| | | | |
|---|---|---|---|
| 3,330,838 | 7/1967 | Augstein et al. | 260/309.6 |
| 3,812,157 | 5/1974 | Lin et al. | 260/345.2 |
| 3,953,506 | 4/1976 | Spicer et al. | 260/553 |
| 4,238,501 | 12/1980 | Kabbe et al. | 424/283 |
| 4,251,537 | 2/1981 | Evans | 424/267 |
| 4,363,811 | 12/1982 | Evans et al. | 424/267 |
| 4,366,163 | 12/1982 | Evans et al. | 424/267 |
| 4,391,815 | 7/1983 | Evans | 424/274 |
| 4,428,881 | 1/1984 | Hedrich et al. | 548/491 |
| 4,481,213 | 11/1984 | Evans | 424/283 |
| 4,568,692 | 2/1986 | Evans | 514/456 |
| 4,571,406 | 2/1986 | Evans et al. | 514/456 |
| 4,575,511 | 3/1986 | Evans et al. | 514/456 |
| 4,602,022 | 7/1986 | Cozzi et al. | 514/337 |
| 4,659,737 | 4/1987 | Kabbe et al. | 514/456 |
| 4,687,779 | 8/1987 | Evans | 514/456 |
| 4,734,421 | 3/1988 | Hammond et al. | 514/274 |
| 4,772,603 | 9/1988 | Evans | 514/241 |
| 4,782,083 | 11/1988 | Cassidy et al. | 514/456 |
| 4,831,050 | 5/1989 | Cassidy et al. | 514/422 |
| 4,904,784 | 2/1990 | Evans et al. | 546/90 |
| 4,925,839 | 5/1990 | Quagliato et al. | 514/212 |
| 4,943,582 | 7/1990 | Evans et al. | 514/320 |
| 4,971,982 | 11/1990 | Attwood et al. | 514/337 |
| 4,988,723 | 1/1991 | Shiokawa et al. | 514/392 |
| 5,006,523 | 4/1991 | Atwal | 514/227.5 |
| 5,011,837 | 4/1991 | Atwal et al. | 514/227.8 |
| 5,013,853 | 5/1991 | Gericke et al. | 549/401 |
| 5,021,432 | 6/1991 | Yamanaka et al. | 514/337 |
| 5,028,711 | 7/1991 | Stenzel et al. | 546/196 |
| 5,053,427 | 10/1991 | Stemp et al. | 514/456 |
| 5,061,813 | 10/1991 | Atwal | 549/399 |
| 5,071,871 | 12/1991 | Blarer et al. | 514/456 |
| 5,082,858 | 1/1992 | Garcia et al. | 514/456 |
| 5,095,016 | 3/1992 | Ohtuka et al. | 514/233.5 |
| 5,096,914 | 3/1992 | Stenzel et al. | 514/392 |
| 5,104,890 | 4/1992 | Shiokawa et al. | 514/370 |
| 5,140,031 | 8/1992 | Atwal et al. | 514/302 |
| 5,143,924 | 9/1992 | Gericke et al. | 514/337 |
| 5,143,936 | 9/1992 | Yamanaka et al. | 514/456 |
| 5,145,985 | 9/1992 | Timar et al. | 548/525 |
| 5,210,234 | 5/1993 | Evans et al. | 549/398 |
| 5,238,937 | 8/1993 | Gericke et al. | 514/253 |
| 5,254,555 | 10/1993 | Stemp et al. | 514/256 |
| 5,268,386 | 12/1993 | Harada et al. | 514/456 |
| 5,276,168 | 1/1994 | Atwal | 549/404 |
| 5,278,169 | 1/1994 | Atwal | 514/302 |
| 5,286,753 | 2/1994 | Schaus et al. | 514/657 |
| 5,310,750 | 5/1994 | Berge et al. | 514/402 |
| 5,310,932 | 5/1994 | Atwal et al. | 548/454 |
| 5,317,029 | 5/1994 | Inazu et al. | 514/422 |
| 5,318,969 | 6/1994 | Yamanaka et al. | 514/247 |
| 5,374,643 | 12/1994 | Atwal et al. | 514/364 |
| 5,393,771 | 2/1995 | Atwal | 514/394 |
| 5,401,848 | 3/1995 | Atwal | 546/153 |

FOREIGN PATENT DOCUMENTS

| | | |
|---|---|---|
| 0076075 | 4/1983 | European Pat. Off. . |
| 0091748 | 10/1983 | European Pat. Off. . |
| 0093535 | 11/1983 | European Pat. Off. . |
| 0120427 | 10/1984 | European Pat. Off. . |
| 0126311 | 11/1984 | European Pat. Off. . |
| 0139992 | 5/1985 | European Pat. Off. . |
| 0205292 | 12/1986 | European Pat. Off. . |
| 0214818 | 3/1987 | European Pat. Off. . |
| 0247266 | 12/1987 | European Pat. Off. . |
| 0250077 | 12/1987 | European Pat. Off. . |
| 0274821 | 7/1988 | European Pat. Off. . |
| 0287196 | 10/1988 | European Pat. Off. . |
| 0339562 | 11/1989 | European Pat. Off. . |
| 0344747 | 12/1989 | European Pat. Off. . |
| 0350805 | 1/1990 | European Pat. Off. . |
| 0351767 | 1/1990 | European Pat. Off. . |
| 0359537 | 3/1990 | European Pat. Off. . |
| 0377966 | 7/1990 | European Pat. Off. . |
| 0377967 | 7/1990 | European Pat. Off. . |
| 0385584 | 9/1990 | European Pat. Off. . |
| 0389861 | 10/1990 | European Pat. Off. . |
| 0401010 | 12/1990 | European Pat. Off. . |
| 0402716 | 12/1990 | European Pat. Off. . |
| 0407200 | 1/1991 | European Pat. Off. . |
| 0412531 | 2/1991 | European Pat. Off. . |
| 0431741 | 6/1991 | European Pat. Off. . |
| 0462761 | 12/1991 | European Pat. Off. . |
| 0488616 | 6/1992 | European Pat. Off. . |
| 0501797 | 9/1992 | European Pat. Off. . |
| 0525768 | 2/1993 | European Pat. Off. . |
| 2801187 | 7/1978 | Germany . |
| 22404868 | 11/1988 | United Kingdom . |
| WO8707607 | 12/1987 | WIPO . |
| WO89/09217 | 10/1989 | WIPO . |
| WO91/09031 | 6/1991 | WIPO . |
| WO92/05174 | 4/1992 | WIPO . |
| WO92/14733 | 9/1992 | WIPO . |
| WO92/22293 | 12/1992 | WIPO . |

OTHER PUBLICATIONS

A.P. Terent'ev et al., "Optically Active Isocynates. III. Synthesis and Spectropolarimetric Study of Optically Active N–derivative of Urea", *Chemical Abstracts*, vol. 71, Abstract No. 69992h, p. 250 (1969).

J. Bermudez et al., "5–Hydroxytryptamine (5–HT$_3$) Receptor Antagonists. 2. 1–Indolinecarboxamides", *J.Med. Chem.*, vol. 33, pp. 1929–1932 (1990).

P.D. Leeson et al., "4–Amido–2–carboxytetrahydroquinolines, Structure–activity Relationships for Antagonism at the Glyncine Site of the NMDA Receptor", *J. Med. Chem.*, vol. 35, pp. 1954–1968 (1992).

J.L. Hughes et al., "Cardiovascular Activity of Aromatic Guanidine Compounds", *J. Med. Chem.*, vol. 18, No. 11, pp. 1077–1088 (1975).

M. Mazza et al., "N–Acilindoline Ad Attivita Fitotossica", *Farmaco. Ed. Sci.,* vol. 31, No. 10, pp. 746–754 (1976).

T. Sekiya et al., "Benzene–condensed Cyclic Amine β–amino Carboxamides as Antichycardiacs and Vasodilators", *Chemical Abstracts,* vol. 113, p. 694 (1990)., No. 171904d.

R. Albrecht et al., "Chemotherapeutic Nitroheterocycles. XI(1). Indanylamides and Indanylesters of 5–nitrofurancarboxylic Acids and Analogous Compounds as Antimicrobial Agents", *Chimie Therapeutique,* vol. 7, No. 1, pp. 9–13 (1972).

H.J. Petersen et al., "Synthesis and Hypotensive Activity of N–Alkyl–N"–cyano–N'–pyridylguanidines", *J. of Med. Chem.,* vol. 21, No. 8, pp. 773–781 (1978).

V.A. Ashwood et al., "Synthesis and Antihypertensive Activity of 4–(Cyclic amido)–2H–benzopyrans", *J. Med. Chem.,* 29, pp. 2194–2201 (1986).

C.R. Rasmussen et al., "Improved Procedures for the Preparation of Cycloalkyl–, Arylalkyl–, and Arylthioureas", *Synthesis,* pp. 456–459 (1988).

V.V. Mozolis et al., "Preparation of N–Substituted Thiourea", *Russian Chem. Reviews.* 42(7), pp. 587–595 (1973).

J.M. Evans et al., "Synthesis and Antihypertensive Activity of Substituted trans–4–Amino–3,4–dihydro–2, 2–dimethyl–2H–1–benzopyran–3–ols", *J. Med. Chem.,* 26, pp. 1582–1589 (1983).

R.W. Lang et al., "Synthesis of Selectivity Trifluoromethylated Pyridine Derivtives as Potential Antipertensives", *Helvetica Chimica Acta,* vol. 71, pp. 596–601 (1988).

P. Sebok et al., "Selective synthesis of Analogues of the Natural Precocenes, Synthesis and Regioselective (–Alkylation of 6–Chloro– and 6–Tert–Butyl–7,8–Dihyedroxy–2, 2–Dimethyl–4–Chromanones", *Heterocycles,* 27, pp. 2595–2607 (1988).

P. Teixidor et al., "Improved Preparation of Precocene II, Unexpected Results in the Reduction of Alkoxy Substituted Acetophenones and 4–Chromanones with Sodium Borohydride", *Heterocycles,* 27, pp. 2459–2465 (1988).

A. Banerji et al., "Enolates of O–Hydroxyacetophenones: Novel Synthesis of 2,2–Dialkyl–4–Chromanones", *Tetrahedron Letter,* No. 38, pp. 3685–2686 (1979).

G. Ariamala et al., "A Simple Route for the Synthesis of 4–Chlorochromanones and Chroman–4–one"*Tetrahedron Letters,* 29, No. 28, pp. 3487–3488 (1988).

*Primary Examiner*—Richard L. Raymond
*Attorney, Agent, or Firm*—Burton Rodney

[57] ABSTRACT

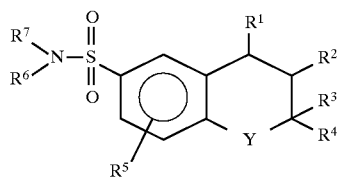

and pharmaceutically acceptable salts thereof wherein Y is a single bond, —$CH_2$—, —C(O)—, —O—, —S— or —N($R^{14}$)—; and $R^1$ to $R^7$ are as defined herein. These compounds have potassium channel activating activity and are useful, therefore for example, as cardiovascular agents.

6 Claims, No Drawings

SULFONAMIDO SUBSTITUTED BENZOPYRAN DERIVATIVES

BRIEF DESCRIPTION OF THE INVENTION

In accordance with the present invention novel compounds having potassium channel activating activity which are useful, for example, as cardiovascular agents, are disclosed. These compounds have the general formula

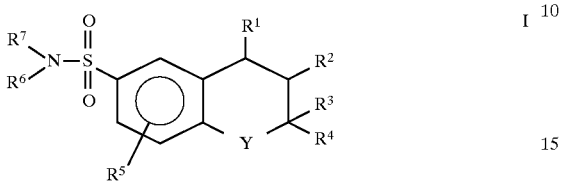

wherein

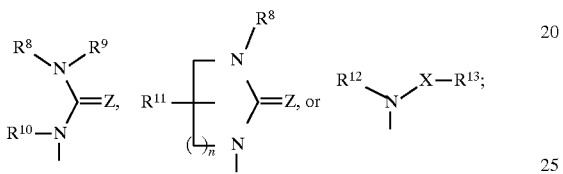

$R^1$ is $R^2$ is hydrogen, hydroxy, or —OC(O)$R^{14}$;

$R^3$ and $R^4$ are each independently hydrogen, alkyl or arylalkyl; or $R^3$ and $R^4$ taken together with the carbon atom to which they are attached form a 3- to 7-membered carbocyclic ring;

$R^5$ is hydrogen, alkyl, halogen, heterocyclo, nitrile, haloalkyl or aryl;

$R^6$ and $R^7$ are independently hydrogen, alkyl, cycloalkyl, aryl, arylalkyl, haloalkyl, hydroxyalkyl, hydroxyalkyl substituted with a carboxylic ester or carboxylic acid, alkoxyalkyl, thioalkyl, (cycloalkyl)alkyl, morpholinylalkyl, heterocyclo or (heterocyclo)alkyl;

or $R^6$ and $R^7$ taken together with the nitrogen atom to which they are attached form a 5- to 7-membered mono or bicyclic ring including fused rings such as 1-pyrrolidinyl, 1-piperidinyl, 1-azepinyl, 4-morpholinyl, 4-thiamorpholinyl, 4-thiamorpholine dioxide, 1-piperazinyl, 4-alkyl-1-piperazinyl, 4-arylalkyl-1-piperazinyl, 4-diarylalkyl-1-piperazinyl; or 1-piperazinyl, 1-pyrrolidinyl, 1-piperidinyl or 1-azepinyl substituted with one or more alkyl, alkoxy, alkylthio, halo, trifluoromethyl, hydroxy, aryl, arylalkyl, —COO$R^{14}$ or —CO-substituted amino;

or $R^5$ and $R^6$ taken together with the atoms to which they are attached form a 5- to 7-membered ring optionally substituted with aryl;

$R^8$ is aryl, arylalkyl, heterocyclo or (heterocyclo)alkyl;

$R^9$ is hydrogen or alkyl;

or $R^8$ and $R^9$ taken together with the nitrogen atom to which they are attached form 1-pyrrolidinyl, 1-piperidinyl, 1-azepinyl, 4-morpholinyl, 4-thiamorpholinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R^{10}$ and $R^{11}$ are independently hydrogen, alkyl, alkenyl, aryl, arylalkyl, cycloalkyl or cycloalkylalkyl; or $R^{11}$ can be an aryl group fused to 2 carbon atoms of the cyanoguanidine ring portion;

$R^{12}$ is aryl or heterocyclo;

$R^{13}$ is —COO$R^{14}$, —CO-amino, —CO-substituted amino, amino, substituted amino, —N$R^{14}$CO-amino, —N$R^{14}$CO-substituted amino, —N$R^{14}$CO$R^{15}$, —N$R^{14}$SO$_2R^{15}$, —N$R^{14}$(C=NCN)-amino, —N$R^{14}$(C=NCN)-substituted amino,

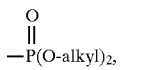

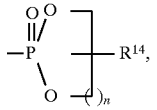

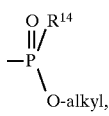

—S$R^{14}$, —SO$R^{14}$, —SO$_2R^{14}$, —O$R^{14}$, cyano, heterocyclo, pyridine-N-oxide, —CH(O$R^{14}$)$_2$,

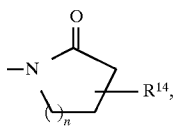

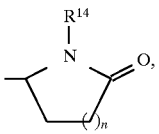

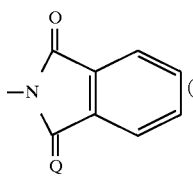 (where Q is O or H$_2$) or

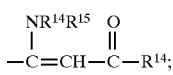

$R^{14}$ and $R^{15}$ are independently hydrogen, alkyl, haloalkyl, aryl, arylalkyl, cycloalkyl or (cycloalkyl)alkyl;

X is alkyl; or X—$R^{13}$ together can be hydrogen, aryl or heterocyclo when $R^{12}$ is heterocyclo;

Y is a single bond, —CH$_2$—, —C(O)—, —O—, —S— or —N($R^{14}$)—;

Z is NCN, S or O; and n is an integer of 1 to 3.

The compounds of this invention possess antiischemic activity and are useful, for example as cardiovascular agents.

DETAILED DESCRIPTION OF THE INVENTION

The invention relates to the sulfonamido compounds of formula I above, to compositions and the methods of using such compounds. The compounds of formula I are useful, for example, as cardiovascular agents.

Listed below are definitions of various terms used to describe the compounds of the instant invention. These definitions apply to the terms as they are used throughout the specification (unless they are otherwise limited in specific instances either individually or as part of a larger group).

The term "alkyl" refers to both straight and branched chain groups having 1 to 8 carbon atoms preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups optionally substituted with one or more substituents selected from halogen, alkoxy, aryl, alkylaryl, haloaryl, cycloalkyl, (cycloalkyl)alkyl, hydroxy, alkylamino, alkyl-substituted amino, alkanoylamino, arylcarbonylamino, nitro, cyano, thiol, alkylthio or —COOR$^{14}$.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups having at least 2 carbon atoms further containing at least one carbon to carbon double bond.

The term "alkynyl" refers to any of the above alkyl groups having at least 2 carbon atoms further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl or 2-naphthyl; phenyl, 1-naphthyl or 2-naphthyl, mono-substituted with ($C_1$–$C_4$)-alkyl, ($C_1$–$C_4$)-alkylthio, ($C_1$–$C_4$)-alkoxy, halo, nitro, cyano, hydroxy, amino, (alkyl)amino, alkyl-substituted amino, —NH—($C_1$–$C_4$)-alkyl, —N( ($C_1$–$C_4$)-alkyl)$_2$, heterocyclo, —CF$_3$, —OCHF$_2$,

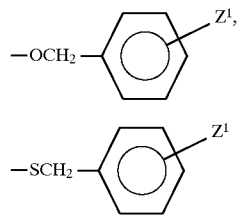

(where $Z^1$ is hydrogen, ($C_1$–$C_4$)-alkyl, ($C_1$–$C_4$)-alkylthio, ($C_1$–$C_4$)-alkoxy, halo, hydroxy or —CF$_3$), —O—CH$_2$-cycloalkyl, or —S—CH$_2$-cycloalkyl; or phenyl, 1-naphthyl or 2-naphthyl, di-substituted with methyl, methoxy, methylthio, halo, —CF$_3$, nitro, amino, —OCHF$_2$, carboxylic acid or carboxylic ester. The term "aryl" also includes those groups listed above fused to a five- or six-membered ring which optionally contains an O, S or N atom (the nitrogen atom being substituted by hydrogen, alkyl, alkoxy, hydroxy, amino, substituted amino, —NHCOR$^{14}$, —CN or —NO$_2$). Preferred aryl groups include unsubstituted phenyl and monosubstituted phenyl wherein the substituents are ($C_1$–$C_4$)-alkyl, methoxy, halo, nitro, cyano or —CF$_3$.

The term "heterocyclo" or "hetero" refers to fully saturated or unsaturated rings of 5 or 7 atoms containing one or two oxygen and/or sulfur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl, imidazolyl, thiazole, oxazole, pyrazole, isoxazole and isothiazole. The term "hetero" also includes bicyclic rings wherein the five- or six-membered ring containing oxygen and/or sulfur and/or nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term "heterocyclo" or "hetero" also includes such monocyclic and bicyclic rings wherein an available carbon atom is substituted with a ($C_1$–$C_4$)-alkyl, aryl, ($C_1$–$C_4$)-alkylthio, ($C_1$–$C_4$)-alkoxy, halo, nitro, keto, cyano, hydroxy, azo, thiazo, amino, —NH—($C_1$–$C_4$)-alkyl, —N(($C_1$–$C_4$)-alkyl)$_2$, —CF$_3$, (aminoester)alkyl, carboxylic acid, carboxylic ester, —OCHF$_2$ or ($C_1$–$C_4$)-alkoxy further substituted with a carboxylic acid or such monocyclic and bicyclic rings wherein two or three available carbons have substituents selected from methyl, methoxy, methylthio, halo, —CF$_3$, nitro, hydroxy, amino and —OCHF$_2$.

The term "substituted amino" refers to a group of the formula —NZ$^2$Z$^3$ wherein Z$^2$ is hydrogen, alkyl, cycloalkyl, aryl, arylalkyl, (cycloalkyl)alkyl, morpholinylalkyl, heterocyclo or (heterocyclo)alkyl and Z$^3$ is hydrogen, alkyl, cycloalkyl, aryl, arylalkyl, haloalkyl, hydroxyalkyl, alkoxyalkyl, thioalkyl, (cycloalkyl)alkyl or hydroxyalkyl further substituted with a carboxylic ester or carboxylic acid, with the proviso that when Z$^2$ is hydrogen, then Z$^3$ is other than hydrogen; or Z$^2$ and Z$^3$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4diarylalkyl-1-piperazinyl; or 1-pyrrolidinyl, 1-piperidinyl, 1-azepinyl substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$)-alkyl- or aryl-sulfonic acids which are unsubstituted or substituted, for example by halogen, for example methane- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine.

Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The below described processes can utilize racemates, enantiomers or diastereomers as starting materials. When diastereomeric products are prepared, they can be separated by conventional methods for example, chromatographic or fractional crystallization. Preferred compounds are those with the 3R or 4S stereochemistry.

It should be understood that the present invention includes prodrug forms of the compounds of formula I such as alkylesters of acids.

The compounds of the instant invention may, for example, be in the free or hydrate form, and may be obtained by methods exemplified by the following descriptions.

Preparation of Compounds of Formula IA

Compounds of formula

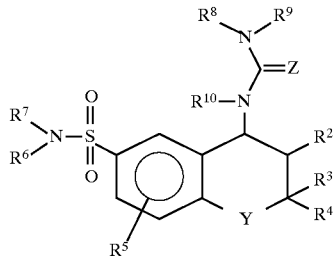

i.e. compounds of formula I where $R^1$ is

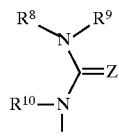

and Z is NCN are prepared by treatment of a thiourea of the formula

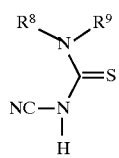

with an amine of the formula

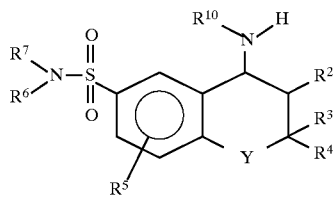

in the presence of a coupling agent, such as a carbodiimide, in a solvent, such as dimethylformamide, tetrahydrofuran, acetonitrile or dichloromethane. Preferably, the carbodiimide is of the formula

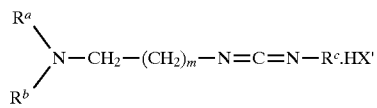

wherein X' halogen, $R^a$, $R^b$ and $R^c$ are independently alkyl, cycloalkyl, phenyl, phenylalkyl, cycloalkylalkyl or $R^a$ and $R^b$ together with the nitrogen atom to which they are attached form 1-pyrrolidinyl, 1-piperidinyl, 4-morpholinyl, 4-thiamorpholinyl, 4-alkyl-1-piperazinyl or 4-phenylalkyl-1-piperazinyl. Most preferably the carbodiimide of formula IV is 1-(3-dimethylaminopropyl)-3-ethylcarbodiimide hydrochloride.

The compounds of formula IA where Z is NCN can also be prepared by reacting an amine of formula III with diphenylcyanocarbonimidate to produce a compound of the formula

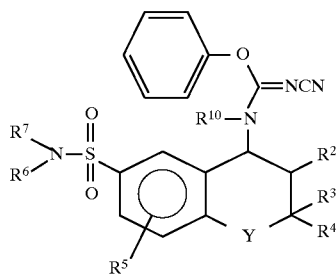

Reaction of a compound of formula V with an amine of the formula

in a polar solvent such as isopropanol produces the compounds of formula IA (where Z is NCN).

Compounds of the formula IA where Z is oxygen or sulfur can be prepared by reacting an amine of the formula III with a compound of formula

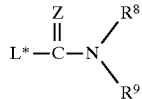

where L* is a leaving or activating group in an organic solvent such as dimethylformamide, tetrahydrofuran, acetonitrile or dichloromethane. Suitable leaving or activating groups include chlorine, 4-nitrophenyloxy and phenoxy.

Compounds of formula 1A where Z is oxygen or sulfur and $R^9$ is hydrogen can be made by reacting amine III with a compound of formula

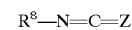

where Z is oxygen or sulfur.

The thiourea of formula II, wherein $R^9$ is hydrogen can be prepared by heating an isothiocyanate of the formula

   IX with either monosodium cyanamide or with cyanamide in the presence of an organic base, such as triethylamine.

The other thioureas of formula II can be prepared by standard methods described in the literature, such as by C. R. Rasmussen et al., Synthesis, p. 456 (1988), and V. V. Mozolis et al., Russian Chemical Reviews, 42, p. 587 (1973).

The amino alcohol of formula III where $R^2$ is hydroxyl can be prepared from 4-hydroxybromobenzene by methods described in the literature such as J. M. Evans et al., J. Med. Chem., 26, 1582 (1983) and J. Med. Chem., 29, 2194 (1986); R. W. Lang et al., Helvetica Chimica Acta, 71, 596 (1988); EP 0205292 (1986); WO 87/07607; and K. S. Atwal et al., J. Med. Chem., 36, 3971 (1993) to form the bromides of formula

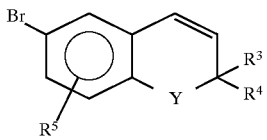   X where Y is oxygen. Successive treatments of the bromides of formula X with n-butyllithium, liquid sulfur dioxide and sulfuryl chloride produces sulfonyl chlorides of formula

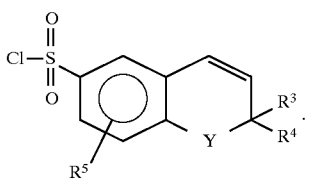   XI

Treatment of the sulfonylchlorides of formula XI with an amine of formula

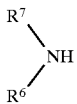   XII in an organic solvent in the presence of a base such as triethylamine or diisopropylethylamine produces the olefins of formula

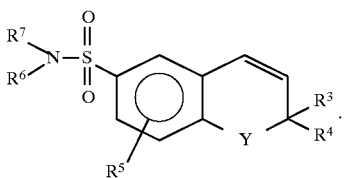   XIII

Epoxidation of the olefins of formula XIII with commercial bleach, m-peroxylchlorobenzoic acid or dimethyldioxirane in the presence of a chiral manganese catalyst of formula

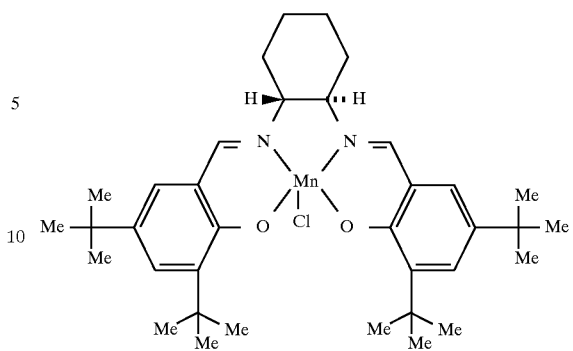   XIV as described by N. H. Lee, et al., Tetrahedron Letters, 32, p. 5055–5058 (1991), produces the epoxides of formula

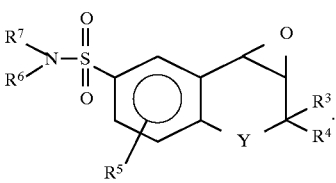   XV

Either enantiomer of epoxide XV can be prepared depending on the chirality of catalyst XIV or racemic mixtures of formula XIV can be obtained by treatment with m-peroxylchlorobenzoic acid in an organic solvent such as dichloromethane. Subsequent treatment of the epoxide of formula XV with an amine of formula $R^{10}NH_2$   XVI or ammonium hydroxide in an organic solvent such as tetrahydrofuran or ethanol produces the amino alcohol of formula III, where $R_2$ is hydroxyl.

Compounds of formula III where $R^2$ is hydrogen, can be prepared from compounds of formula XIII by a sequence of steps which involve (a) catalytic hydrogenation (b) radical bromination and (c) displacement of bromide with an amine of formula XVI.

Compounds of formula X wherein Y is —O— can be prepared according to Tetrahedron Letters, 35, p. 6405–6408 (1994) and references cited therein.

Compounds of formula X wherein Y is a single bond or —N($R^{14}$)— can be prepared according to D. R. Buckle, et al., J. Med. Chem., 34, p. 919 (1991).

Compounds of formula X wherein Y is —CH$_2$— can be prepared by methods described in V. A. Ashwood, et al., J. Med. Chem., 34, p. 3261 (1991).

Compounds of formula X wherein Y is —C(O)— may be prepared by methods described by C. Almansa et al., J. Med. Chem., Vol. 36, p. 2121–2133 (1993).

Compounds of formula X wherein Y is —S— can be prepared according to the methods described by D. Smith et al., EP-0322251.

The compounds formula IA where Z is sulfur can be prepared by converting a compound of formula III by standard methods (i.e., the Rasmussen and Mozolis references cited above) to a thiourea of the formula

XVII

Subsequent heating with monosodium cyanamide in the presence of a carbodiimide such as 1-(3-dimethylaminopropyl)-3-ethylcarbodiimide or dicyclohexylcarbodiimide in an organic solvent produces the compounds of formula IA (where Z is S).

Most of the compounds of formula IV, VI, IX, XII and XVI are commercially available or can be prepared by standard methods described in text books of organic chemistry such as Introduction to Organic Chemistry by A. Streitwieser and C. H. Heathcock, Macmillan Publishing Co., Inc., N.Y. (1976).

Preparation of Compounds of Formula IB

The compounds of formula

IB i.e. compounds of the formula I wherein $R^1$ is and Z is NCN can be prepared by treating a diamine of the formula

XVIII with dimethyl-N-cyanodithioiminocarbonate to form compounds of the formula

XIX

Subsequent treatment with mercuric acetate in an alcoholic solvent such as methanol produces the compounds of formula IB (where Z is NCN).

Compounds of formula IB wherein Z is oxygen or sulfur can be prepared from compounds of formula XVIII by treatment with phosgene (thiophosgene) or p-nitrophenylchloroformate in the presence of an organic base such as pyridine or triethylamine.

The compounds of formula IB where Z is NCN can also be prepared by treating a diamine of formula XVIII with diphenylcyano-carbonimidate in an alcoholic solvent, such as 2-propanol.

The compounds of formula XVIII wherein $R^2$ is trans hydroxyl are obtained by treatment of an epoxide of formula XV with a diamine of the formula

XX in an alcoholic solvent, such as ethanol.

Compounds of formula XVIII can also be prepared from the amine III and an alkylating agent of the formula

XXI wherein P is a protecting group such as a phthalamido group and X" is a leaving group, such as Cl, Br or I, in the presence of a base catalyst, such as potassium carbonate followed by deprotection.

The compounds of formula IB wherein $R^2$ is —$OCOR^{14}$ can be prepared by acylation of the alcohols of formula IB, (where $R^2$ is hydroxyl), with an acid chloride of the formula

XXII in the presence of a base catalyst, such as pyridine or triethylamine.

Most of the compounds of formula VII, VIII, XX, XXI and XXII are commercially available, or they can be readily prepared by methods described in standard text books of organic chemistry, for example, Introduction to Organic Chemistry by A. Streitwieser and C. H. Heathcock, Macmillan Publishing Co., Inc. N.Y. (1976); and Advanced Organic Chemistry by F. C. Carey and R. J. Sundberg, Plenum Publishing Co., N.Y. (1977).

Preparation of Compounds of Formula IC

Compounds of formula

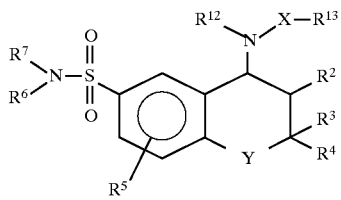   IC where $R^2$ is trans-hydroxy and X is —$CH_2$—, can be prepared by first reacting an epoxide of formula XV with an amine of formula $R^{12}$—$NH_2$   XXIII under heat or preferably in the presence of a Lewis acid such as magnesium perchlorate or trimethylaluminum to provide an intermediate of formula

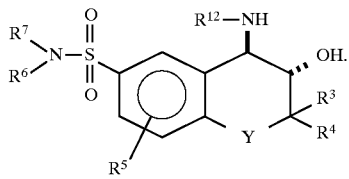   XXIV

The intermediate of formula XXIV is then derivatized by reductive amination using an aldehyde of formula $$\underset{HCR^{13}}{\overset{O}{\|}}$$   XXV in the presence of a reducing agent such as sodium cyanoborohydride or sodium triacetoxyborohydride. Alternatively, reductive amination can be effected with hydrogen gas in the presence of a catalyst such as palladium on carbon.

Compounds of formula IC can also be prepared by reacting an epoxide of formula XV with an amine of formula $R^{12}$—NH—X—$R^{13}$   XXVI in an organic solvent such as acetonitrile in the presence of a Lewis acid such as magnesium perchlorate or cobalt chloride.

Compounds of formula IC wherein $R^2$ is hydroxyl, can also be prepared by treatment of an epoxide of formula XV with an anion or dianion of the compound of formula XXVI. The anion or dianion of compound XXVI can be prepared by treatment of the amine of formula XXVI with a strong base (n-butyl lithium, potassium hexamethyldisilazide etc.) in an organic solvent such as tetrahydrofuran.

Compounds of formula IC wherein $R^{13}$ is CO-amino or CO-substituted amino, can be prepared by reacting compounds of formula IC wherein $R^{13}$ is $COOR^{14}$ with ammonia or an appropriate amine.

Compounds of formula IC where $R^{13}$ is $NR^{14}$CO-amino, $NR^{14}$CO-substituted amino, $NR^{14}COR^{15}$, $NR^{14}SO_2R^{15}$, $NR^{14}$(C=NCN)-amino or $NR^{14}$(C=NCN)-substituted amino can be prepared from compounds of formula IC where $R^{13}$ is amino or substituted amino by methods described in the literature such as those used for acylation, urea formation, sulfonylation and cyanoguanidine formation of organic chemistry, for example, Introduction to Organic Chemistry by A. Streitwieser and C. H. Heathcock, Macmillan Publishing Co., Inc. N.Y. (1976), and Advanced Organic Chemistry by F. C. Carey and R. J. Sundberg, Plenum Publishing Co., N.Y. (1977).

Compounds of formula IC where $R^{12}$ is heterocyclo (e.g., benzoxazole) and $R^2$ is trans-hydroxy can also be prepared by first reacting an epoxide of formula XV with an amine of formula $H_2N$—X—$R^{13}$   XXVII under heat or in the presence of a Lewis acid such as magnesium perchlorate or trimethylaluminum to provide an intermediate of formula

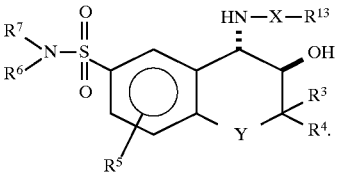   XXVIII

The intermediate of formula XXVIII is then reacted with a heterocycle containing a leaving group (e.g., 2-chlorobenzoxazole) in the presence of a base such as sodium hydride in an organic solvent such as tetrahydrofuran or dimethylformamide to form compounds of formula IC where $R^{12}$ is heterocyclo and $R^2$ is trans-hydroxy.

Other compounds of formula IC wherein $R^{12}$ is heterocyclo (e.g., oxazole, pyrazole, isoxazole etc.) can be prepared from intermediates of formula XXVIII by standard methods.

Compounds of formula IC wherein $R^{12}$ is heterocyclo (e.g., thiazole) can also be prepared by alkylation of a compound of formula XXIV with an alkylating agent of formula

L'—X—$R^{13}$   XXIV where L' is a leaving group such as a halogen, mesylate or tosylate.

Compounds of formula IC wherein $R^2$ is hydrogen can be prepared from compounds of formula

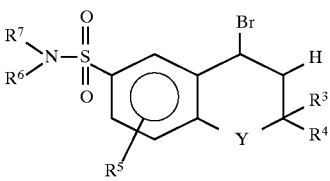   XXX by reaction with an amine of formula XXVI in the presence of a base such as sodium hydride or potassium carbonate.

Alternatively, compounds of formula IC where $R^2$ is hydrogen can be prepared by first reacting a compound of formula XXX with an amine of formula III in the presence of a base (e.g., sodium hydride) to provide a compound of formula

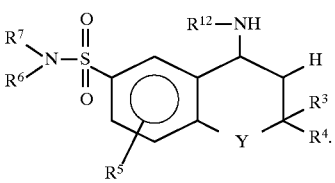   XXXI

The compound of formula XXXI is then converted to compounds of formula IC where $R^2$ is hydrogen by methods described for the conversion of compounds of formula XXIV to compounds of formula IC. Compounds of formula XXXI where $R^2$ is hydrogen can also be prepared from compounds of formula XXIV by (a) dehydration of the alcohol with sodium hydride in aprotic solvents such as tetrahydrofuran; and (b) catalytic hydrogenation or reductive amination by sodium cyanoborohydride or sodium triacetoxyborohydride.

Compounds of formula IC where $R^2$ is $-OC(O)R^{14}$ can be prepared from compounds of formula IC where $R^2$ is hydroxy by treatment with an acid chloride of formula XXII in the presence of a base catalyst such as pyridine or triethylamine.

Compounds of formula XXVI are prepared by reductive amination of an amine of formula XXIII with an aldehyde of formula XXV in the presence of a reducing agent such as sodium borohydride, sodium cyanoborohydride and sodium triacetoxyborohydride.

Compounds of formula XXX are prepared from compounds of formula XIII by a sequence of steps which involves catalytic reduction of the double bond followed by radical bromination.

Most of the compounds of formula XXIII, XXV, XXVII and XXIX are commercially available or they can be prepared by standard methods described in text books of organic chemistry such as Introduction to Organic Chemistry by A. Streitwieser and C. H. Heathcock, Macmillan Publishing Co., Inc. N.Y. (1976), and Advanced Organic Chemistry by F. C. Carey and R. J. Sundberg, Plenum Publishing Co., N.Y. (1977).

All other compounds of formula I may be prepared by modification of the procedures discussed herein as known by those having ordinary skill in the art. The intermediates used to prepare compounds of formula I are described herein, are commercially available, or may be derived from known compounds by those having ordinary skill in the art or may be prepared by literature methods or derived by procedures analagous to those described in the literature.

The compounds of the present invention can have asymmetric centers at carbons 2–4 of the benzopyran ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The compounds of the formula IA wherein $R^9$ and/or $R^{10}$ is hydrogen, can exist as a mixture of tautomers represented by the following structures. The tautomeric products are obtained in relative amounts that differ from compound to compound. All forms are included in the scope of formula I.

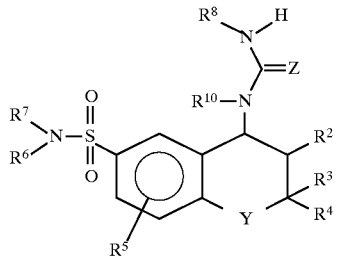

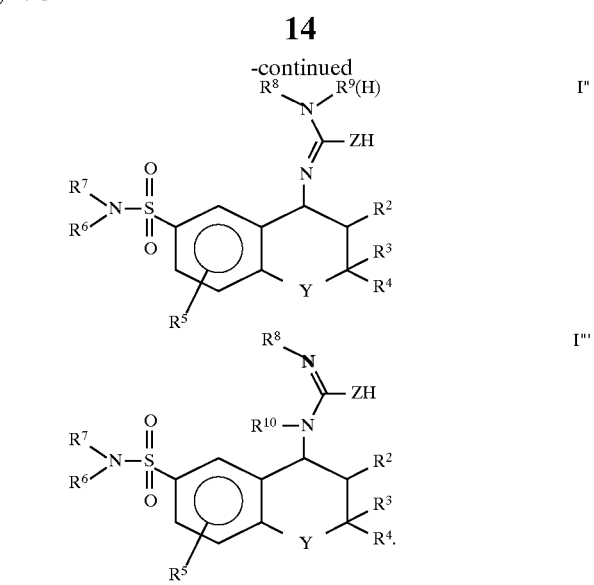

The compounds of the present invention can have asymmetric centers at carbons 2–4 of the bicyclic ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by methods known in the art such as conventional chromatographic or fractional crystallization methods.

If any of the R substituents, X or Y groups contain reactive groups such as hydroxy or amino that can interfere with the epoxide opening reaction or any other reactions, they should be protected with appropriate protecting groups.

The compounds of formula I are unexpectedly more potent than those described previously. In addition it has been unexpectedly found that compounds of formula I are "selective antiischemic agents". The term "selective antiischemic agent" means that these compounds possess little or no vasodilator activity (i.e., these compounds have $IC_{50}$ (rat aorta) values greater than that of the known potassium channel activator, cromakalim). Therefore, in the treatment of ischemic hearts, the compounds of the instant invention are less likely to cause coronary steal, profound hypotension and coronary under-perfusion.

The preferred compounds of the present invention are those compounds of formula IA and IB where:

Y is oxygen;
$R^2$ is hydroxyl;
$R^3$ and $R^4$ are methyl;
$R^6$ and $R^7$ are alkyl; or $R^6$ and $R^7$ taken together with the nitrogen atom to which they are attached form a 6-membered ring;
$R^8$ is aryl or heterocyclo;
$R^9$ is hydrogen;
$R^{10}$ is hydrogen; and
$R^{11}$ is hydrogen.

Compounds of formula IC are preferred where:
X is alkyl;
Y is a single bond or —O—;
$R^2$ is hydroxy;
$R^3$ and $R^4$ are methyl;
$R^{12}$ is aryl or heterocyclo; and
$R^{13}$ is —$COOR^{14}$, —CO-amino, —CO-substituted amino, —$NHCOCH_3$, —$NHSO_2Me$, —$NHCONH_2$, —NH(C=NCN)NH₂, imidazole, furan, pyridine, oxazole, hydroxy, —NHCO-substituted amino or —SO₂Me; or XR¹³ is hydrogen.

Compounds of formula I may be used as antiischemic agents, i.e., for the treatment of ischemic conditions such as myocardial ischemia, cerebral ischemia, lower limb ischemia and the like.

Thus a composition containing one (or a combination) of the compounds of this invention, may be administered to a species of mammal (e.g., humans) suffering from an ischemic or hypertensive condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the potassium channel activating activity of the compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents, and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, for the treatment of male impotence, as well as for the promotion of hair growth (e.g., in the treatment of male pattern baldness), and as anti-asthmatic agents.

The compounds of this invention can also be formulated in combination with a diuretic such as chlorothiazide, hydrochlorothiazide, flumethiazide, hydroflumethiazide, bendroflumethiazide, methylchlothiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

(3S-transs)-N-(4-Chlorophenyl)-N'-cyano-N"-[6-[(diethylamino)sulfonyl]-3,4-dihydro-3-hydroxy-2,2-dimethyl-2H-1-benzopyran-4-yl]guanidine

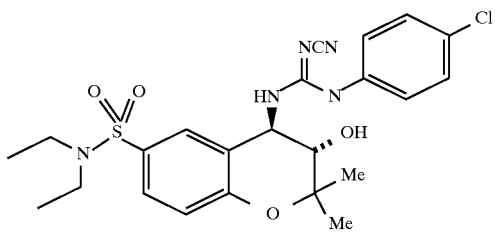

A. 1-Bromo-4-[(1,1-dimethyl-2-propynyl)oxy]benzene

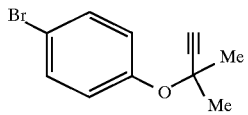

To a solution of 2-methyl-3-butyn-2-ol (22.3 mL, 0.23 mol) in acetonitrile (100 mL) at −2° C. (dry-ice, ice-water) was added 1,8-diazabicyclo[5,4,0]undec-7-ene (DBU, 40 mL, 0.26 mol), followed by drop-wise addition of trifluoroacetic acid anhydride (32 mL, 0.23 mol) via syringe over 30 minutes. The resultant yellow solution was stirred at 0° C. for 40 minutes. In a separate 1 L round bottomed flask, a solution of 4-bromophenol (34.6 g, 0.2 mol) in acetonitrile (150 mL) at 0° C. was treated with 1,8-diazabicyclo[5,4,0]undec-7-ene (DBU, 39 mL, 0.26 mol), followed by addition of 100 mg of CuCl₂. To this mixture at 0° C. was added the above prepared solution via a cannula in 40 minutes. The resultant reaction mixture was stirred at 0° C. for 5 hours, and at room temperature for 1 hour. The reaction mixture was then concentrated in vacuo and the residue was poured into water (300 mL). The aqueous solution was extracted with a mixture of hexane and ether (300 mL, 1:1). The organic extract was washed successively with 1N HCl (200 mL), 1N KOH (2×100 mL) and saturated NaCl solution. The organic layer was then dried over MgSO₄ and concentrated to give a yellow oil (40 g, 83%).

B. 6-Bromo-2,2-dimethyl-2H-1-benzopyran

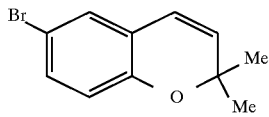

To 40 mL of N,N-diethylaniline at 185° C. (internal, monitored by a thermal couple) was added 1-bromo-4-[(1,1-dimethyl-2-propynyl)oxy]benzene (40 g, the title A compound) dropwise at such a rate that the internal temperature does not exceed 195° C. (approximately 1 hour). The resultant solution was stirred at 185° C. for 3 hours and poured into a mixture of hexanes (200 mL) and chilled 4% HCl (200 mL) in a beaker. The mixture was transferred to a separatory funnel and the organic layer was separated, and washed with 5% HCl (2×100 mL). The organic layer was then dried over MgSO$_4$ and concentrated in vacuo to give an oil (40 g, 100%). Anal. Calc. for C$_{11}$H$_{11}$BrO: C, 55.98; H, 4.92; Br, 32.58. Found: C, 55.95; H, 4.61; Br, 32.44.

C. 2,2-Dimethyl-2H-1-benzopyran-6-sulfinic acid, lithium salt

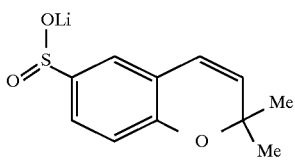

To a stirred solution of 6-bromo-2,2-dimethyl-2H-1-benzopyran (8.0 g, 33.6 mmol, the title B compound) in anhydrous THF (75 mL) at −78° C. under argon was added a solution of n-BuLi in hexanes (2.5M, 15 mL, 37.5 mnol) via syringe. The resultant solution was stirred at −78° C. for 30 minutes and added to a solution of sulfur dioxide (35 mL, condensed at −78° C.) in anhydrous ether (150 mL) at −78° C. via a double-ended needle. The resultant mixture was allowed to stir at −78° C. for 10 minutes and allowed to warm up to room temperature over an hour. The resultant solution was concentrated in vacuo to give a light yellow solid which was triturated with hexanes to give the title compound as a solid (7.5 g, 91%).

D. 2,2-Dimethyl-2H-1-benzopyran-6-sulfonyl chloride

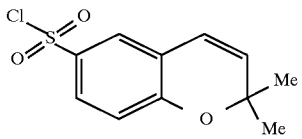

To a vigorously stirred suspension of 2,2-dimethyl-2H-1-benzopyran-6-sulfinic acid, lithium salt (7.5 g, 33 mmol, the title C compound) in hexanes (150 mL) at 0° C. under argon was added a solution of sulfuric chloride (5.0 g, 37 mmol) in hexanes (50 mL) in 3 portions over one minute. The light yellow suspension became a clear solution soon after addition of the sulfuric chloride; resulting eventually in the formation of a white precipitate. The resultant suspension was stirred at 0° C. for 15 minutes and the precipitate was collected. The filtrate was concentrated in vacuo to a small volume and cooled to −78° C. The precipitate thus formed was collected. The combined solid was dissolved in toluene (100 mL) and the solution was washed with pH 7.0 potassium phosphate buffer followed by brine. The organic layer was dried over MgSO$_4$ and concentrated and the residue was triturated with pentane to give a white solid. The mother liquor was cooled to −78° C. and the precipitate was collected to give a solid for a total of 5.4 g (63%), mp 79°–81° C. Anal. Calc. for C$_{11}$H$_{11}$ClSO$_3$.0.13H$_2$O: C, 50.61; H, 4.35; Cl, 13.58; S, 12.28. Found: C, 50.61; H, 4.19; Cl, 13.80; S, 11.99.

E. N,N—Diethyl-2,2-dimethyl-2H-1-benzopyran-6-sulfonamide

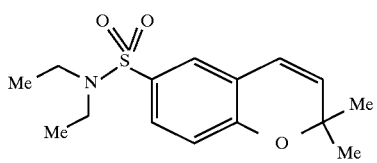

To a stirred solution of diethylamine (1.5 g, 20.5 mmol) in a mixture of water and CH$_2$Cl$_2$ (1:1; v/v; 20 mL) at 0° C., was added 2,2-dimethyl-2H-1-benzopyran-6-sulfonyl chloride (1.0 g, 3.9 mmol, the title D compound) portionwise. The resultant mixture was stirred at 0° C. for 20 minutes and room temperature for 2 hours. The organic layer was separated and the aqueous layer was reextracted with CH$_2$Cl$_2$ (2×50 mL). The combined organic extracts were dried, concentrated in vacuo to give the title compound as an oil (1.12 g, 100%).

F. (1aS-cis)-N,N-Diethyl-1a,7b-dihydro-2,2-dimethyl-2H-oxireno[c][1]benzopyran-6-sulfonamide

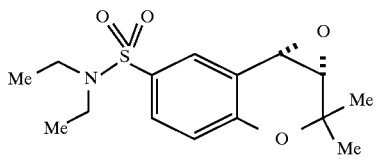

Commercial Clorox bleach (15.0 mL, 0.705M, 10.5 mmol) was diluted with Na$_2$HPO$_4$ buffer (6 mL, 50 mM) in a single neck round-bottom flask. The pH of the mixture was adjusted to 11.3 by addition of 1N NaOH (drops) at 0° C. In a separate flask, the solution of N,N-diethyl-2,2-dimethyl-2H-1-benzopyran-6-sulfonamide (1.1 g, 3.7 mmol, the title E compound) in CH$_2$Cl$_2$ (15 mL) was treated with the Jacobsen's catalyst [(salem)Mn(II)] (30 mg, about 1.0 mol%, described by Lee et al, *Tetrahedron Letters*, 32, 5055 (1991)), followed by 4-phenylpyridine-N-oxide (20 mg). This resultant solution was stirred at room temperature for 30 minutes and at 0° C. for 30 minutes. It was then mixed with the buffered Chlorox solution prepared above. The resultant biphasic mixture was stirred at 0° C. for 18 hours, poured into methylene chloride (50 mL) and the organic layer was separated. The aqueous layer was extracted with methylene chloride (2×50 mL) and the combined organic extracts were washed with saturated NH$_4$Cl solution and brine (25 mL each). After drying over MgSO$_4$, the solvent was removed in vacuo to give the title F compound as an oil (1.05 g, 91%).

G. (3S-trans)-4-Amino-N,N-diethyl-3,4-dihydro-3-hydroxy-2,2-dimethyl-2H-1-benzopyran-6-sulfonamide

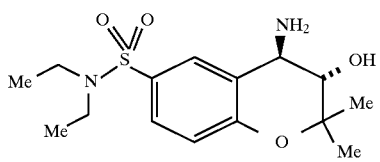

To a stirred solution of (1aS-cis)-N,N-diethyl-1a,7b-dihydro-2,2-dimethyl-2H-oxireno[c][1]benzopyran-6-sulfonamide (910 mg, 2.5 mmol, the title F compound) in a mixture of THF and isopropanol (15 mL, 2:1, v/v) was added conc. NH$_4$OH (3 mL) and the reaction mixture was heated in a sealed tube at 75° C. (oil bath temperature) for 24 hours. The reaction mixture was cooled to room temperature and concentrated in vacuo. The residue was diluted with ethyl acetate (100 mL) and extracted with saturated NaHCO₃. The organic layer was dried, concentrated in vacuo and the residue was crystallized from ethyl acetate-cyclohexane to give a white solid (850 mg, 70%). [α]_D^25: +50.9° (c=0.90, MeOH).

H. (3S-trans)-N-(4-Chlorophenyl)-N'-cyano-N"-[6-[(diethylamino)sulfonyl]-3,4-dihydro-3-hydroxy-2,2-dimethyl-2H- 1-benzopyran-4-yl]guanidine

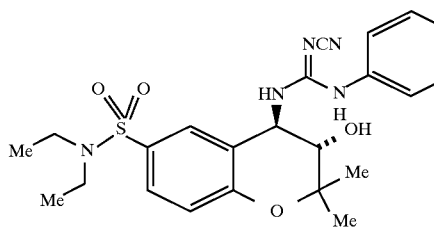

To a stirred solution of (3S-trans)-4-amino-N,N-diethyl-3,4-dihydro-3-hydroxy-2,2-dimethyl-2H-1-benzopyran-6-sulfonamide (400 mg, 1.2 mmol, the title G compound) and N-chlorophenyl-N'-cyanothiourea (283 mg, 1.34 mmol) in DMF (7 mL) was added 1-[3-(dimethylamino)propyl]-3-ethylcarbodiimide hydrochloride (257 mg, 1.34 mmol) at room temperature under argon. The reaction mixture was stirred at room temperature for 18 hours. The resultant mixture was poured into a mixture of ethyl acetate (100 mL) and saturated NH₄Cl solution (50 mL). The ethyl acetate layer was separated and the aqueous layer was reextracted with ethyl acetate (2×50 mL). The combined organic layer was washed with brine (50 mL). After drying over MgSO₄, the solvent was removed and the residue was purified by flash chromatography (ethyl acetate:hexane/1:1) to give a colorless solid after trituration with ether (400 mg, 65%), mp: 125° C. (shrink); 164° C. (melts). [α]_D^25: +7.8° (c=0.60, CH₃OH). Anal. Calc. for C₂₃H₂₈N₅O₄SCl.0.26 H₂O.0.15C₇H₈(toluene): C, 55.03; H, 5.71; N, 13.34; S, 6.11; Cl, 6.75. Found: C, 55.03; H, 5.64; N, 13.02; S, 5.97; Cl, 6.97.

EXAMPLE 2

(3S-trans)-N-(4-Chlorophenyl)-N'-cyano-N"-[3,4-dihydro-3-hydroxy-2,2-dimethyl-6-[(4-piperidinylsulfonyl)-2H-1-benzopyran-4-yl]guanidine

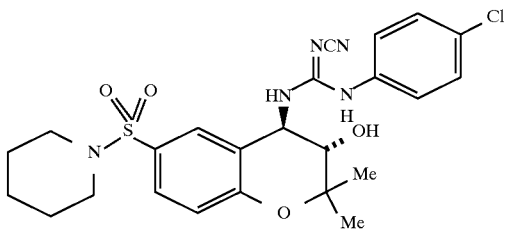

The title compound was prepared by the same procedure as described for the title compound of Example 1. The product was obtained as a white solid (mp: 174° C.). [α]_D^25: 18° (c=0.25, MeOH). Anal. Calc. for C₂₄H₂₈N₅O₄SCl.0.20 H₂O: C, 55.26; H, 5.49; N, 13.43. Found: C, 55.11; H, 5.47; N, 13.41.

EXAMPLE 3

(3S-trans)-N-(4-Chlorophenyl)-N'-cyano-N"-[3,4-dihydro-3-hydroxy-2,2-diimethyl-6-[(4-morpholinyl)sulfonyl]2H-1-benzopyran-4-yl]guanidine

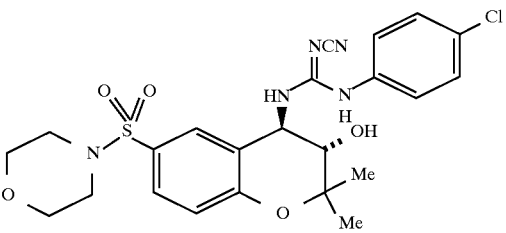

The title compound was prepared by the same procedure as described for the title compound of Example 1. The product was obtained as a white solid (mp: 160° C.). [α]_D^25: +27.2° (c=0.60, CH₃OH). Anal. Calc. for C₂₃H₂₆N₅O₅SCl.0.36H₂O: C, 52.47; H, 5.12; N, 13.30; S, 6.09; Cl, 6.73. Found: C, 52.54; H, 5.23; N, 13.23; S, 5.90; Cl, 6.99.

EXAMPLE 4

(3S-trans)-N-(4-Chlorophenyl)-N"-cyano-N'-[3,4-dihydro-3hydroxy-2,2-dimethyl-6-[[(phenylmethyl)amino]sulfonyl]-2H-1-benzopyran-4-yl)guanidine

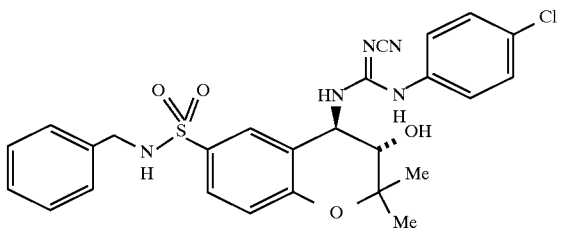

The title compound was prepared by the same procedure as described in Example 1. The product was obtained as a white solid (mp: 140° C.). [α]_D^25: +50.0° (c=0.40, CH₃OH). Anal. Calc. for C₂₆H₂₆N₅O₄SCl: C, 57.83; H, 4.85; N, 12.97; S, 5.94; Cl, 6.56. Found: C, 58.18; H, 4.99; N, 11.63; S, 5.86; Cl, 6.67.

EXAMPLE 5

(3S-trans )-N-(4-Chlorophenyl)-N'-cyano-N"-[6-[(cyclohexylamino)sulfonyl]-3,4-dihydro-3-hydroxy-2,2-dimethyl-2H- 1-benzopyran-4-yl]guanidine

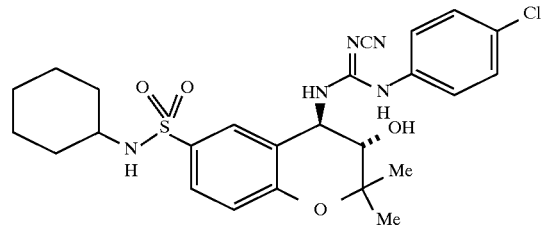

The title compound was prepared by the same procedure as described for the title compound of Example 1. The product was obtained as a white solid (mp: 165° C.). [α]_D^25: +3.5° (c=1.3, CH₃OH). Anal. Calc. for $C_{25}H_{30}N_5O_4SCl.0.64H_2O$ C, 55.24; H, 5.80; N, 12.88; S, 5.90; Cl, 6.52. Found: C, 55.62; H, 5.88; N, 12.50; S, 5.64; Cl, 6.79.

EXAMPLE 6

(3S-trans)-1-[4-[[[(4-Chlorophenyl)amino](cyanoimino) methyl]amnino]-3,4-dihydro-3-hydroxy-1-2H-benzopyran-6-yl]sulfonyl]-2-piperidinecarboxylic acid, ethyl ester

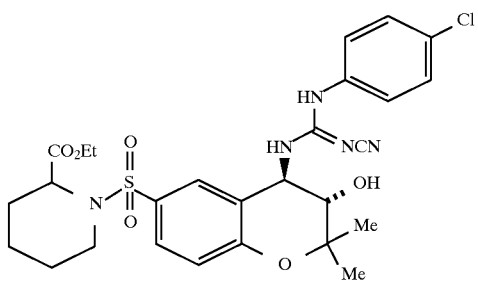

The title compound was prepared by the same procedure as described for the title compound of Example 1. The product was obtained as a white solid (mp: 95° C.). Anal. Calc. for $C_{27}H_{32}N_5O_6SCl.0.6DMF.0.5H_2O$: C, 53.80; H, 5.83; N, 12.20; S, 4.99; Cl, 5.51. Found: C, 53.58; H, 5.80; N, 12.05; S, 4.82; Cl, 5.87.

EXAMPLE 7

(3S-trans)-N-(4-Chlorophenyl)-N'-cyano-N"-[3,4-dihydro-3-hydroxy-2,2-dimethyl-6-[(phenylamino)sulfonyl]-2H-1-benzopyran-4-yl]guanidine

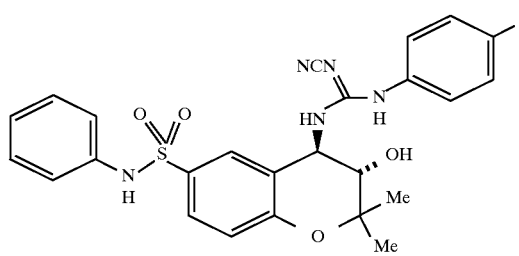

The title compound was prepared by the same procedure as described for the title compound of Example 1. The product was obtained as a white solid (mp: 158° C.). Anal. Calc. for $C_{25}H_{24}N_5O_4SCl.1.54H_2O$: C, 54.13; H, 5.10; N, 12.63; S, 5.78; Cl, 6.39. Found: C, 54.57; H, 4.86; N, 12.19; S, 5.59; Cl, 7.88.

EXAMPLE 8

(3S-trans)-N-(4-Chlorophenyl)-N'-cyano-N"-[3,4-dihydro-3-hydroxy-2,2-dimethyl-6-[[2-(phenylmethyl)-1-piperidinyl) sulfonyl]-2H-1 benzopyran-4-yl]guanidine

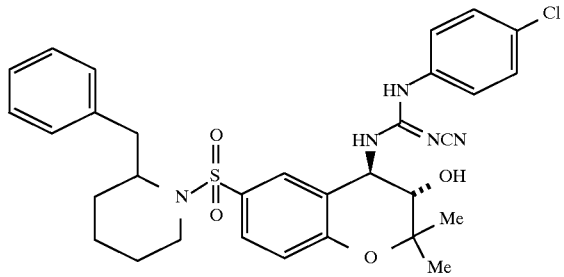

The title compound was prepared by the same procedure as described for the title compound of Example 1. The product was obtained as a white solid (mp: 105° C.). Anal. Calc. for $C_{31}H_{34}N_5O_4SCl.0.70H_2O.0.40DMF$: C, 59.50; H, 5.92; N, 11.64; S, 4.93; Cl, 5.45. Found: C, 59.53; H, 6.05; N, 11.95; S, 4.70; Cl, 5.17.

EXAMPLE 9

(3S-trans)-N-(4-Chlorophenyl)-N'-cyano-N"-[3,4-dihydro-3-hydroxy-2,2-dimethyl-6-[(2-phenyl-1-piperidinyl)sulfonyl]-2H-1 -benzopyran-4-yl] guanidine

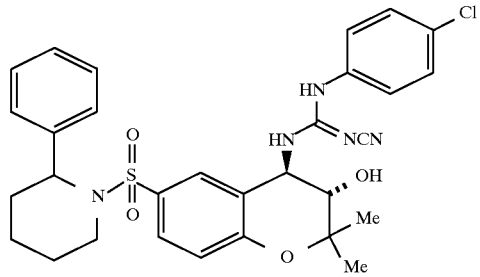

The title compound was prepared by the same procedure as described for the title compound of Example 1. The product was obtained as a white solid (mp: 143° C.). Anal. Calc. for $C_{30}H_{32}N_5O_4SCl.0.26H_2O$: C, 60.17; H, 5.47; N, 11.69; S, 5.35; Cl, 5.92. Found: C, 59.89; H, 5.77; N, 11.95; S, 5.41; Cl, 5.49.

EXAMPLE 10

(3S-trans)-N-(4-Chlorophenyl)-N'-cyano-N"-[3,4-dihydro-3-hydroxy-2,2-dimethyl-6-[[4-(phenylmethyl)-1-piperidinyl]-sulfonyl]-2H-1-benzopyran-4-yl]guanidine

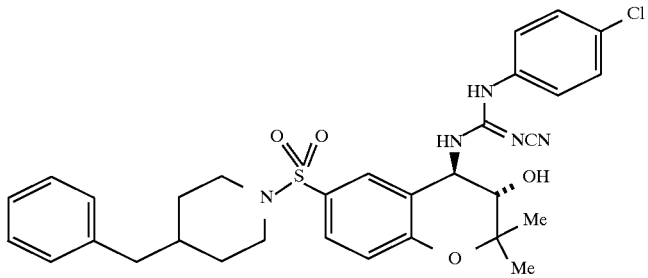

The title compound was prepared by the same procedure as employed for the preparation of the Example 1 by using 4-benzylpiperidine for diethylamine. The title compound was obtained as a white solid (mp: >200° C.). Anal. Calc. for $C_{31}H_{34}N_5O_4SCl$: C, 61.22; H, 5.63; N, 11.52; S, 5.27; Cl, 5.83. Found: C, 61.07; H, 5.64; N, 11.36; S, 5.19; Cl, 5.88.

EXAMPLE 11

(3S-trans)-1-[[4-[[[(4-Chlorophenyl)amino](cyanoimino)-methyl]amino]-3,4-dihydro-3-hydroxy-2,2-dimethyl-2H-1-benzopyran-6-yl]sulfonyl]-N-ethyl-2-piperidine-carboxamide

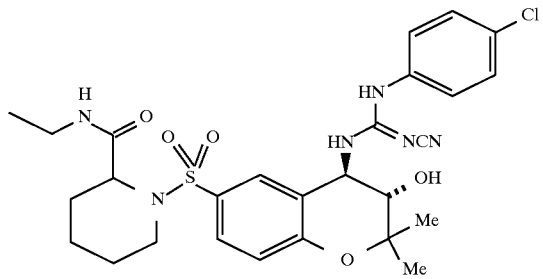

The title compound was prepared by the same procedure as described for the title compound of Example 1. The product was obtained as a white solid [mp: 170° C. (foams)]. Anal. Calc. for $C_{27}H_{33}N_6ClSO_5$: C, 55.05; H, 5.65; N, 14.27; Cl, 6.02; S, 5.49. Found: C, 55.07; H, 5.81; N, 14.08; Cl, 6.36; S, 5.44.

EXAMPLE 12

(3S-trans)-[N-[[4-[[[(4-Chlorophenyl)amino](cyanoimino)-methyl]amino]-3,4-dihydro-3-hydroxy-2,2-dimethyl-2H-1-benzopyran-6-yl]sulfonyl]phenylamino]acetic acid, ethyl ester

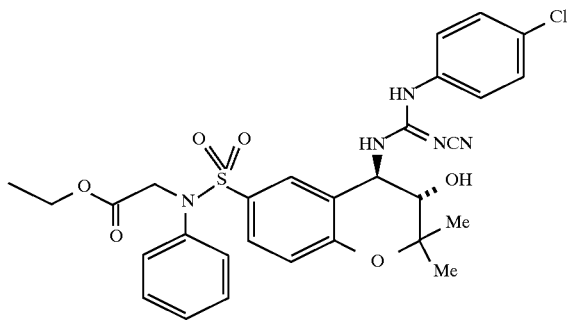

The title compound was prepared by the same procedure as described for the title compound of Example 1. The product was obtained as a light yellow solid (mp: 158° C.). Anal. Calc. for $C_{29}H_{30}N_5O_6SCl \cdot 0.37H_2O$: C, 56.29; H, 5.01; N, 11.32; S, 5.18; Cl, 5.73. Found: C, 56.47; H, 4.99; N, 11.14; S, 5.46; Cl, 6.16.

EXAMPLE 13

(3S-trans)-N-(3-Chlorophenyl)-N'-[6-[(diethylamino)-sulfonyl]-3,4-dihydro-3-hydroxy-2,2-dimethyl-2H-1-benzopyran-4-yl]urea

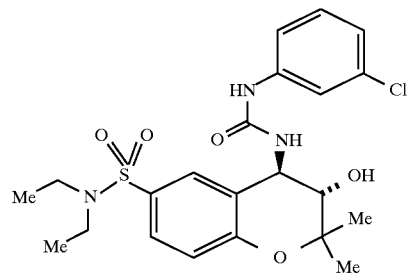

To a stirred solution of the title G compound of Example 1 (148 mg, 0.45 mmol) in 10 mL of $CH_2Cl_2$ in the presence of 1 mL of saturated $NaHCO_3$, was added 3-chlorophenyl-isocyanate (70 mL, 0.53 mmol) at 0° C. The reaction mixture was allowed to stir at 0° C. for 10 minutes. Work up with 10% aqueous KOH solution gave the title compound as a crystalline solid (135 mg, 62%, mp: 202°–203° C.). Anal. Calc. for $C_{22}H_{28}N_3O_5SCl$: C, 54.82; H, 5.86; N, 8.72; S, 6.65. Found: C, 54.40; H, 5.90; N, 8.59; S, 6.53.

EXAMPLE 14

(3S-trans)-N-(4-Chlorophenyl)-N'-cyano-N"-[6-[(2-ethyl-1-piperidinyl)sulfonyl]-3,4-dihydro-3-hydroxy-2,2-dimethyl-2H-1-benzopyran-4-yl]guanidine

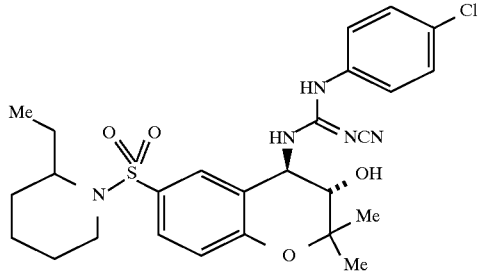

The title compound was prepared by the same procedure as described for the title compound of Example 1. The product was obtained as a tan solid (mp: 158° C.). Anal. Calc. for $C_{26}H_{32}N_5O_4SCl.0.45H_2O$: C, 56.35; H, 5.98; N, 12.64; S, 5.79; Cl, 6.40. Found: C, 56.68; H, 6.12; N, 12.29; S, 5.90; Cl, 6.49.

EXAMPLE 15

(7S-trans)-N-(4-Chlorophenyl)-N'-cyano-N"-(3,6,7,8-tetrahydro-7-hydroxy-6,6-dimethyl-2-phenyl-2H-pyrano-[2,3-f]-benzisothiazol-8-yl)guanidine, 1,1-dioxide

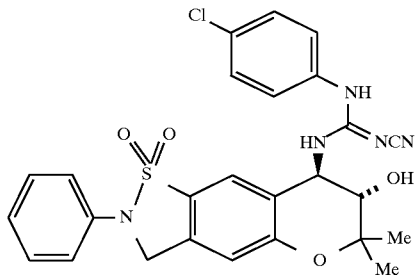

The title compound was prepared by the same procedure as described for the title compound of Example 1. The product was obtained as a white solid (mp: 230°–232° C.). Anal. Calc. for $C_{26}H_{24}N_5O_4SCl.0.44H_2O$: C, 57.20; H, 4.59; N, 12.83; Cl, 6.49; S, 5.87. Found: C, 57.32; H, 4.21; N, 12.70; Cl, 6.67; S, 5.83.

EXAMPLE 16 trans-N-(4-Chlorophenyl)-N'-cyano-N"-N-[3,4-dihydro-3-hydroxy-2,2-dimethyl-6-[(3-pyridinylamino)sulfonyl]-2H-1-benzopyran-4-yl]guanidine

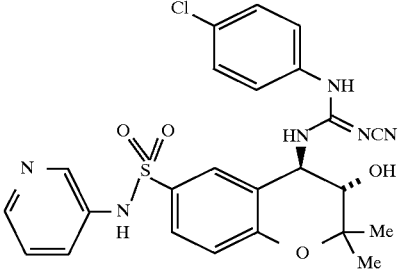

The title compound was prepared by the same procedure as described for the title compound of Example 1. The product was obtained as a light yellow solid (mp: 165° C.). Anal. Calc. for $C_{24}H_{23}N_6O_4SCl.0.39H_2O$: C, 53.98; H, 4.49; N, 15.74. Found: C, 53.98; H, 4.21; N, 15.75.

EXAMPLE 17

(3S-trans)-N-(4-Chlorophenyl)-N'-cyano-N"-N-[3,4-dihydro-3-hydroxy-2,2- dimethyl-6-[[(2-phenylethyl) (3-pyridinylmethyl)amino]sulfonyl]-2H-1-benzopyran-4-yl]guanidine

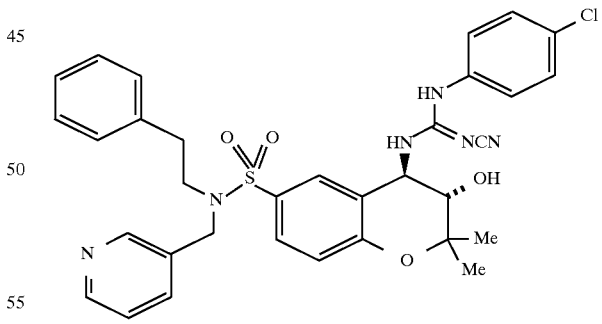

The title compound was prepared by the same procedure as described for the title compound of Example 1. The product was obtained as a white solid (mp: 110° C.). Anal. Calc. for $C_{33}H_{33}N_6O_4SCl.0.4H_2O$: C, 60.75; H, 5.22; N, 12.89; S, 4.91; Cl, 5.43. Found: C, 61.00; H, 5.00; N, 12.29; S, 5.14; Cl, 5.77.

EXAMPLE 18

(3S-trans)-N-(4-Chlorophenyl)-N'-cyano-N"-N-[6-[[(2,2-dimethylpropyl) (2-phenylethyl) amino]sulfonyl]-3,4-dihydro-3-hydroxy-2,2-dimethyl-2H-1-benzopyran-4-yl]guanidine

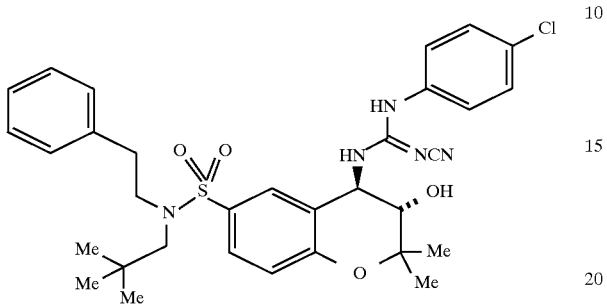

The title compound was prepared by the same procedure as described for the title compound of Example 1. The product was obtained as a white solid (mp: 143° C.). Anal. Calc. for $C_{32}H_{38}N_5O_4SCl$: C, 61.58; H, 6.14; N, 11.22; S, 5.14; Cl, 5.68. Found: C, 61.54; H, 6.30; N, 11.02; S, 5.07; Cl, 5.48.

EXAMPLE 19

(3S-trans)-N-(4-Chlorophenyl)-N'-cyano-N"-[6-[[ethyl(2-phenylethyl)amino]sulfonyl]-3,4-dihydro-3-hydroxy-2,2-dimethyl-2H 1-benzopyran-4-yl]guanidine

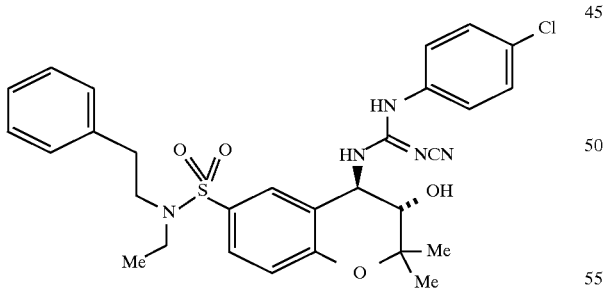

The title compound was prepared by the same procedure as employed for the preparation of the Example 1 by using ethyl 2-phenylethyl amine for diethylamine. The title compound was obtained as a white solid (mp: 127°–131° C.). Anal. Calc. for $C_{29}H_{32}N_5O_4SCl$: C, 59.86; H, 5.54; N, 12.03; S, 5.51; Cl, 6.09. Found: C, 60.05; H, 5.69; N, 11.64; S, 5.32; Cl, 5.84.

EXAMPLE 20

(3S-trans)-N-(4-Chlorophenyl)-N'-cyano-N"-[3,4-dihydro-3. hydroxy-2,2-dimethyl-6-[(3-methyl-1-piperidinyl)sulfonyl]-2H-1-benzopyran-4-yl]guanidine

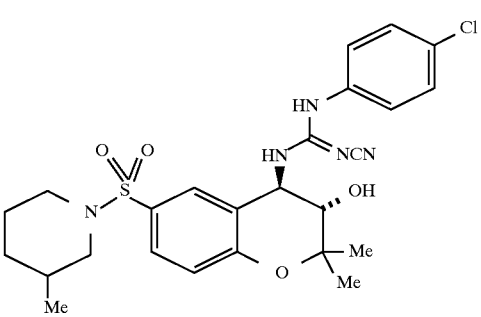

The title compound was prepared by the same procedure as described for the title compound of Example 1. The product was obtained as a white solid (mp: 175° C.). Anal. Calc. for $C_{25}H_{30}N_5O_4SCl.0.52H_2O$ C, 55.46; H, 5.78; N, 12.94; S, 5.92; Cl, 6.55. Found: C, 55.57; H, 5.69; N, 12.66; S, 5.86; Cl, 6.56.

EXAMPLE 21

(3S-trans)-N-(4-Chlorophenyl)-N'-cyano-N"-[3,4-dihydro-3-hydroxy-2,2-dimethyl-6-[(3,3-dimethyl-1-piperidinyl)-sulfonyl]-2H-1-benzopyran-4-yl]guanidine

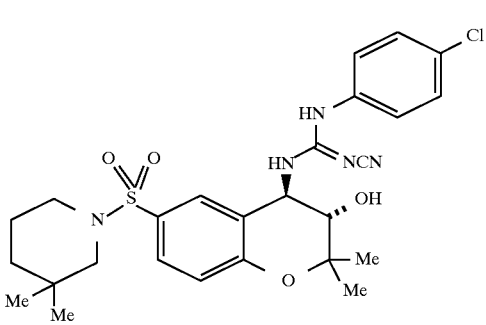

The title compound was prepared by the same procedure as described for the title compound of Example 1. The product was obtained as a white solid (mp: 175° C.). Anal. Calc. for $C_{26}H_{32}N_5O_4SCl.0.31H_2O$ C, 55.61; H, 5.96; N, 12.70; S, 5.81; Cl, 6.43. Found: C, 57.04; H, 6.01; N, 12.27; S, 5.75; Cl, 6.23.

EXAMPLE 22

(3S-trans)-N-(4-Chlorophenyl)-N'-cyano-N''-[3,4-dihydro-3-hydroxy-2,2-dimethyl-6-(1-pyrrolidinylsulfonyl)-2H-1-benzopyran-4-yl]guanidine

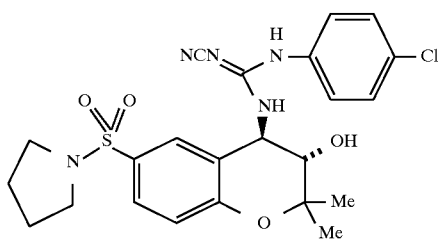

The title compound was prepared by the same procedure as described for the title compound of Example 1. The product was obtained as a white solid (mp: 127°–131° C.). $[\alpha]_D = +7.4°$ (c=0.7, MeOH). Anal. Calc. for $C_{23}H_{26}N_5ClSO_4 \cdot 1.8 H_2O \cdot 0.11 CHCl_3$: C, 50.49; H, 5.49; N, 12.74; S, 5.83; Cl, 8.58. Found: C, 50.20; H, 5.24; N, 13.10; S, 5.65; Cl, 8.99.

EXAMPLE 23

(3S-trans)-N-(4-Chlorophenyl)-N'-cyano-N''-[6-[(hexahydro-1H-azepin-1-yl)sulfonyl]-3,4-dihydro-3-hydroxy-2,2-dimethyl-2H-1-benzopyran-4-yl]guanidine

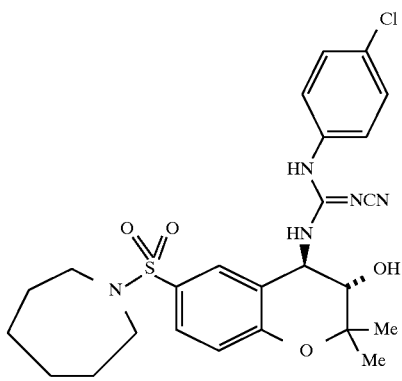

The title compound was prepared by the same procedure as described for the title compound of Example 1. The product was obtained as a white solid (mp: 157°–161° C.). $[\alpha]_D = +1.1°$ (c=0.4, MeOH). Anal. Calc. for $C_{25}H_{30}N_5ClSO_4 \cdot 0.85 H_2O \cdot 0.09 CHCl_3$: C, 53.98; H, 5.77; N, 12.54; S, 5.74; Cl, 8.06. Found: C, 54.36; H, 5.62; N, 12.04; S, 5.71; Cl, 7.67.

EXAMPLE 24

(3S-trans)-N-(4-Chlorophenyl)-N'-cyano-N''-[6-[(ethylphenyl-amino)sulfonyl]-3,4-dihydro-3-hydroxy-2,2-dimethyl-2H-1-benzopyran-4-yl]guanidine

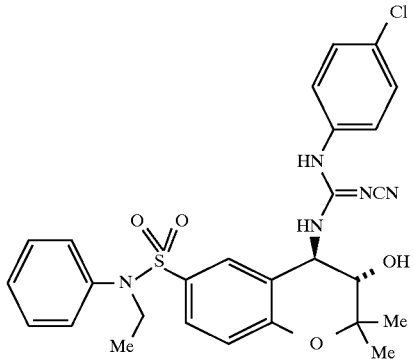

The title compound was prepared by the same procedure as described for the title compound of Example 1. The product was obtained as a white solid (mp: 115°–119° C.). $[\alpha]_D = -11.1°$ (c=0.7, MeOH). Anal. Calc. for $C_{27}H_{28}N_5ClSO_4 \cdot 0.7 H_2O \cdot 0.05 CHCl_3$: C, 53.98; H, 5.77; N, 12.54; S, 5.74; Cl, 8.06. Found: C, 54.36; H, 5.62; N, 12.04; S, 5.71; Cl, 7.67.

EXAMPLE 25

(3S-trans)-1-[4-[[[(4-Chlorophenyl)amino](cyanoimino)-methyl]amino]-3,4-dihydro-3-hydroxy-1-2-benzopyran-6-yl]sulfonyl]-3-piperidinecarboxylic acid, ethyl ester

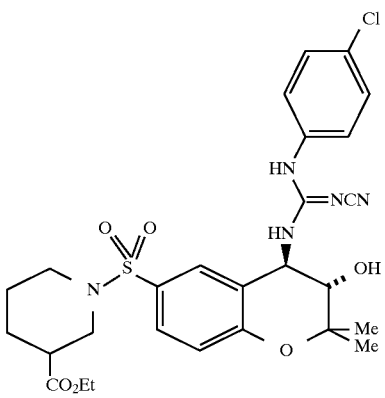

The title compound was prepared by the same procedure as described for the title compound of Example 1. The product was obtained as a white solid (mp: 158°–160° C.). $[\alpha]_D = +6.9°$, (c=0.6, MeOH). Anal. Calc. for $C_{27}H_{32}N_5ClSO_6 \cdot 0.25 H_2O \cdot 0.33 CHCl_3$: C, 51.72; H, 5.32; N, 11.03; S, 5.05; Cl, 11.12. Found: C, 51.89; H, 5.04; N, 10.64; S, 5.29; Cl, 11.22.

EXAMPLE 26

(3S-trans)-4-[4-[[[(4-Chlorophenyl)amino](cyanoimino)-methyl]amino]-3,4-dihydro-3-hydroxy-1-2H-benzopyran-6-yl]sulfonyl]-1-piperazinecarboxylic acid, 1,1-dimethylethyl ester

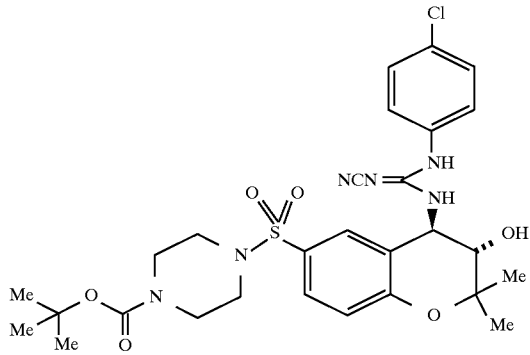

The title compound was prepared by the same procedure as described for the title compound of Example 1. The product was obtained as a white solid (mp: 128°–132° C.). $[\alpha]_D = +11.3°$ (c=0.6, MeOH). Anal. Calc. for $C_{28}H_{35}N_6O_6SCl\cdot0.95\ H_2O$: C, 52.86; H, 5.83; N, 13.21. Found: C, 52.83; H, 5.80; N, 13.23.

EXAMPLE 27

(3S-trans)-N-(4-Chlorophenyl)-N'-cyano-N''-[3,4-dihydro-3-hydroxy-2,2-dimethyl-6-[(4-methyl-1-piperidinyl)sulfonyl]-2H-1-benzopyran-4-yl]guanidine

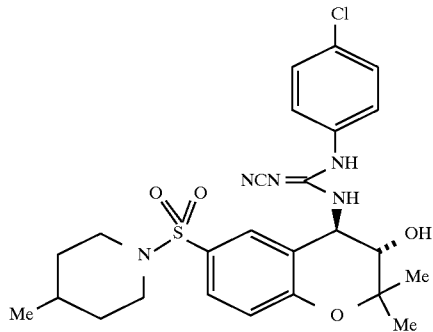

The title compound was prepared by the same procedure as described for the title compound of Example 1. The product was obtained as a white solid (mp: 157°–160° C.). $[\alpha]_D = +12.7°$ (c=0.3, MeOH). Anal. Calc. for $C_{25}H_{30}N_5O_4SCl\cdot0.35\ H_2O$: C, 55.37; H, 5.70; N, 12.89; S, 5.90; Cl, 7.31. Found: C, 55.37; H, 5.61; N, 12.79; S, 5.77; Cl, 7.53.

EXAMPLE 28

(3S-trans)-N-(4-Chlorophenyl)-N'-cyano-N''-[6-[[(cyanomethyl)(2-phenylethyl)amino]sulfonyl]-3,4-dihydro-3-hydroxy-2,2-dimethyl-2H-1-benzopyran-4-yl]guanidine

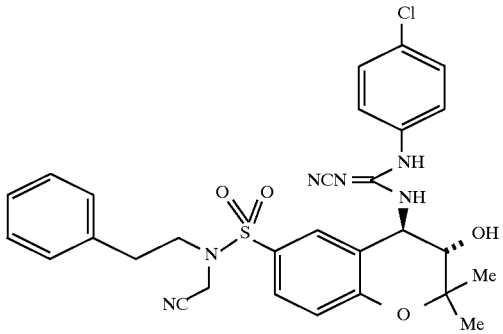

The title compound was prepared by the same procedure as described for the title compound of Example 1. The product was obtained as a white solid (mp: 125°–130° C.). $[\alpha]_D = +27.9°$ (c=0.3, MeOH). Anal. Calc. for $C_{29}H_{29}N_6O_4SCl\cdot0.4\ H_2O\cdot0.24\ CF_3CO_2H$: C, 56.41; H, 4.82; N, 13.39; S, 5.11; Cl, 5.65; F, 2.19. Found: C, 56.35; H, 4.65; N, 13.64; S, 4.84; Cl, 5.33, F, 2.14.

EXAMPLE 29

(3S-trans)-N-(4-Chlorophenyl)-N'-cyano-N''-[6-[[(cyanomethyl)(phenylmethyl)amino]sulfonyl]-3,4-dihydro-3-hydroxy-2,2-dimethyl-2H-1-benzopyran-4-yl]guanidine

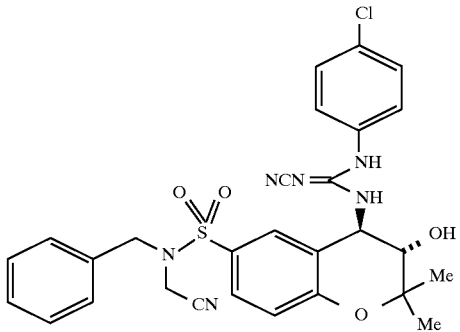

The title compound was prepared by the same procedure as described for the title compound of Example 1. The product was obtained as a white solid (mp: 153°–155° C.). $[\alpha]_D = +60.0°$ (c=0.3, MeOH). Anal. Calc. for $C_{28}H_{27}N_6O_4SCl\cdot0.7\ H_2O\cdot0.05\ CHCl_3$: C, 56.37; H, 4.80; N, 14.06; S, 5.36; Cl, 6.82. Found: C, 56.59; H, 4.59; N, 13.86; S, 5.20; Cl, 6.50.

EXAMPLE 30

(3S-trans)-N-[6-[[Bis(phenylmethyl)amino)sulfonyl]
-3,4-dihydro-3-hydroxy-2,2-dimethyl-2H-1-
benzopyran-4-yl]-N'-(4-chlorophenyl)-N"-
cyanoguanidine

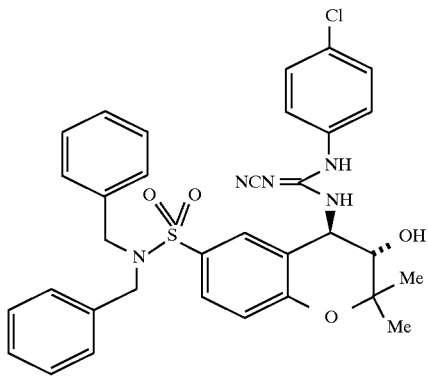

The title compound was prepared by the same procedure as described for the title compound of Example 1. The product was obtained as a white solid (mp: 199°–201° C.). $[\alpha]_D=+68.0°$ (c=0.5, MeOH). Anal. Calc. for $C_{33}H_{32}N_5O_4SCl.0.1\ H_2O.0.05\ CHCl_3$: C, 62.23; H, 5.10; N, 10.98; S, 5.03; Cl, 6.39. Found: C, 62.46; H, 4.85; N, 10.84; S, 4.93; Cl, 6.39.

EXAMPLE 31

[3S-[3a,4b,6(cis)]]-N-(4-Chlorophenyl)-N'-cyano-
N"-[6-[(2,6-dimethyl-1-piperidinyl)sulfonyl]-3,4-
dihydro-3-hydroxy-2,2-dimethyl-2H-benzopyran-
4-yl]guanidine

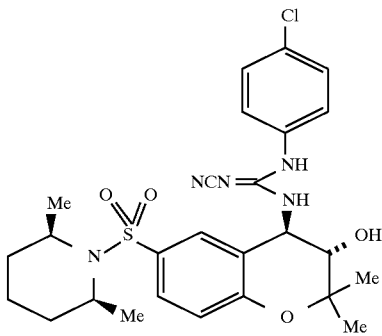

The title compound was prepared by the same procedure as described for the title compound of Example 1. The product was obtained as a white solid (mp: 176°–178° C.). $[\alpha]_D=-15.0°$ (c=0.4, MeOH). Anal. Calc. for $C_{26}H_{32}N_5O_4SCl.0.3\ H_2O.0.25\ CHCl_3.0.1\ EtOAc$: C, 54.24; H, 5.75; N, 11.87. Found: C, 54.60; H, 5.37; N, 11.51.

EXAMPLE 32

(3S-trans)-N-[6-[[Bis (2-methylpropyl)amino]
sulfonyl]-3,4-dihydro-3-hydroxy-2,2-dimethyl-2H-1-
benzopyran-4-yl]-N'-(4-chlorophenyl)-N"-
cyanoguanidine

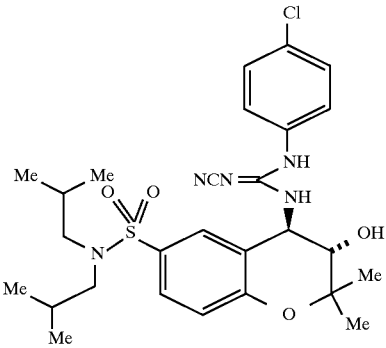

The title compound was prepared by the same procedure as described for the title compound of Example 1. The product was obtained as a white solid (mp: 145°–148° C.). $[\alpha]_D=-0.5°$ (c=0.36, MeOH). Anal. Calc. for $C_{27}H_{36}N_5O_4SCl.0.9\ H_2O$: C, 56.08; H, 6.59; N, 12.11. Found: C, 56.42; H, 6.36; N, 11.76.

EXAMPLE 33

(3S— trans)-N-(4-Chlorophenyl)-N'-cyano-N"-[6-[[
(cyanomethyl)(3-phenylpropyl)amino]sulfonyl]-3,4-
dihydro-3-hydroxy-2,2-dimethyl-2H-1-benzopyran-
4-yl]guanidine

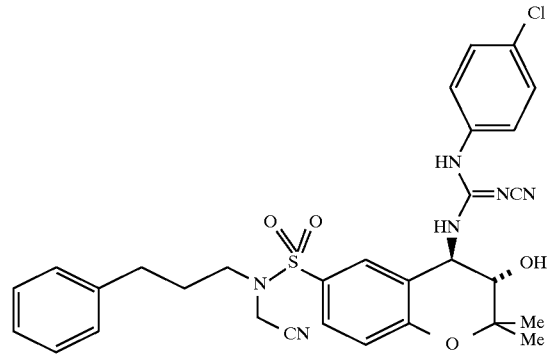

The title compound was prepared by the same procedure as described for the title compound of Example 1. The product was obtained as a white solid (mp: 99°–101° C.). $[\alpha]_D=+20.0°$ (c=0.31, MeOH). Anal. Calc. for $C_{30}H_{31}N_6ClSO_4.1.0\ H_2O.0.10\ CHCl_3$: C, 56.75; H, 5.24; N, 13.19; S, 5.03; Cl, 7.23. Found: C, 56.75; H, 5.32; N, 13.38; S, 4.75; Cl, 7.27.

EXAMPLE 34

N-(4-Chlorophenyl)-N'-cyano-N"-[(3S,4R)-6-[(3,5-dimethyl-1-piperidinyl)sulfonyl]-3,4-dihydro-3-hydroxy-2,2 dimethyl-2H-1-benzopyran-4-yl]guanidine

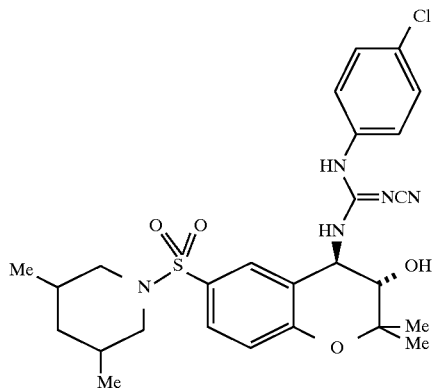

The title compound was prepared by the same procedure as described for the title compound of Example 1. The product was obtained as a white solid (mp: 138°–140° C.). $[\alpha]_D = -4.0°$ (c=0.36, MeOH). Anal. Calc. for $C_{26}H_{32}N_5SClO_4 \cdot 1.70\, H_2O \cdot 0.10\, CHCl_3$: C, 53.26; H, 6.08; N, 11.90; S, 5.45; Cl, 7.83. Found: C, 53.66; H, 5.77; N, 12.14; S, 5.02; Cl, 7.93.

EXAMPLE 35

N-(4-Chlorophenyl)-N'-cyano-N"-[(3S,4R)-3,4-dihydro-3-hydroxy-2,2-dimethyl-6-[[3-(phenylmethyl)-1-piperidinyl)-sulfonyl]-2H-1-benzopyran-4-yl]guanidine

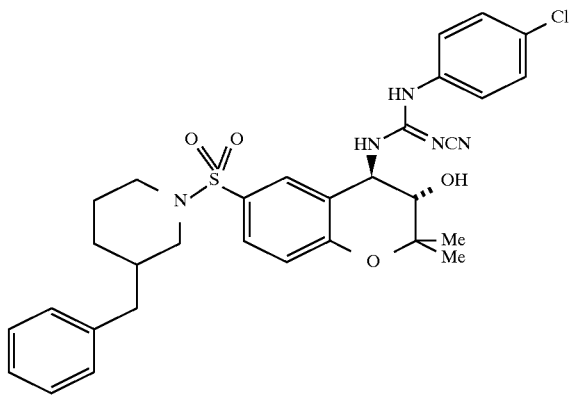

The title compound was prepared by the same procedure as described for the title compound of Example 1. The product was obtained as a white solid (mp: 150° C.). Anal. Calc. for $C_{31}H_{34}N_5O_4SCl$: C, 61.22; H, 5.63; N, 11.52; S, 5.27; Cl, 5.83. Found: C, 61.21; H, 5.66; N, 11.14; S, 5.12; Cl, 6.19.

EXAMPLE 36

(3S-trans)-1-[[4-[[(Cyclohexylamnino)carbonyl]amino]-3,4-dihydro-3-hydroxy-2,2-dimethyl-1-2H-benzopyran-6-yl]sulfonyl]-2-piperidinecarboxylic acid, ethyl ester

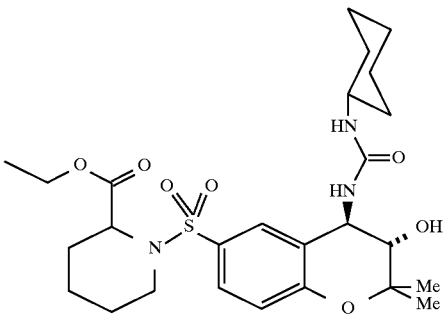

The title compound was prepared by the same procedure as described for the title compound of Example 1. The product was obtained as a white solid (mp: 110° C.). Anal. Calc. for $C_{26}H_{39}N_3O_7S$: C, 58.08; H, 7.31; N, 7.86; S, 5.96. Found: C, 57.92; H, 7.46; N, 7.46; S, 5.86.

EXAMPLE 37

(3S-trans)-1-[[3,4-Dihydro-3-hydroxy-2,2-dimethyl-4-[[[(phenylmethyl)amino]carbonyl]amino]-1-2H-benzopyran-6-yl)sulfonyl]-2-piperidinecarboxylic acid, ethyl ester

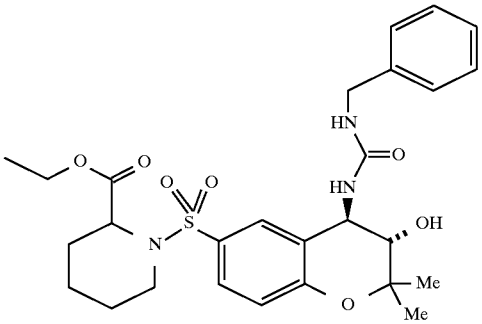

The title compound was prepared by the same procedure as described for the title compound of Example 1. The product was obtained as a white solid (mp: 105° C.). Anal. Calc. for $C_{27}H_{35}N_3O_7S$: C, 59.43; H, 6.47; N, 7.70; S, 5.88. Found: C, 57.06; H, 6.49; N, 7.49; S, 5.99.

EXAMPLE 38

(3S-trans)-1-[[3,4-Dihydro-3-hydroxy-2,2-dimethyl-4-[[(2-thiazolylamino)carbonyl]amino]-1-2H-benzopyran-6-yl]sulfonyl]-2-piperidinecarboxylic acid, ethyl ester

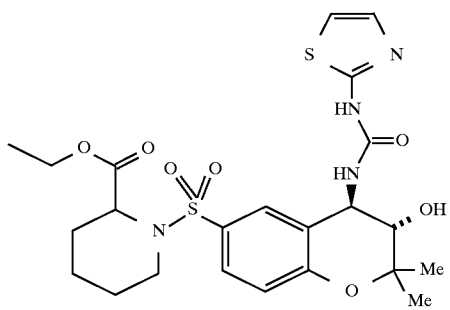

The title compound was prepared by the same procedure as described for the title compound of Example 1. The product was obtained as a yellow solid (mp: 102° C.). Anal. Calc. for $C_{23}H_{30}N_4O_7S_2 \cdot 0.45 C_7H_8$: C, 54.14; H, 5.84; N, 9.66; S, 11.05. Found: C, 54.20; H, 5.85; N, 9.35; S, 10.73.

EXAMPLE 39

(3S-trans)-N-[6-[(3-Azabicyclo[3.2.2]nonan-3-yl)sulfonyl]-3,4-dihydro-3-hydroxy-2,2-dimethyl-2H-1-benzopyran-4-yl]-N'-(4-chlorophenyl)-N"-cyanoguanidine

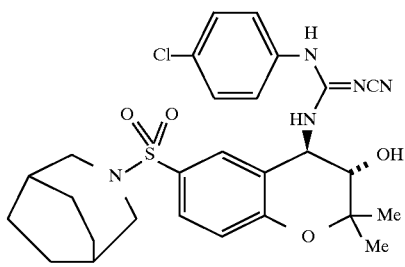

The title compound was prepared by the same procedure as described for the title compound of Example 1. The product was triturated with hot ethyl acetate/hexanes (1:1), mp 213°–216° C. $[\alpha]_D = +7.6°$ (c=0.42, MeOH). Anal. Calc. for $C_{26}H_{22}ClN_5O_3 \cdot 0.40H_2O$: C, 57.36; H, 5.85; N, 12.39; S, 5.67; Cl, 6.27. Found: C, 57.77; H, 5.80; N, 11.98; S, 5.68; Cl, 6.26. m/s, MH+@ 488, MW=487.

EXAMPLE 40

(3S-trans)-N-(4-Chlorophenyl)-N'-cyano-N"-[3,4-dihydro-3-hydroxy-2,2-dimethyl-6-[(1,2,3,4-tetrahydro-1-quinolinyl)sulfonyl]-2H-1-benzopyran-4-yl]guanidine

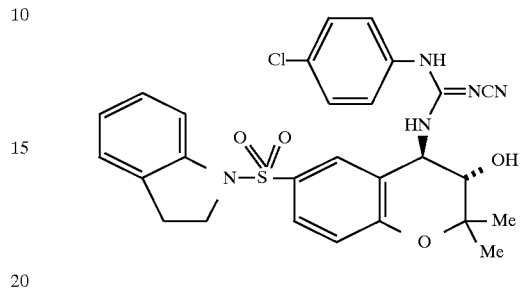

The title compound was prepared by the same procedure as described for the title compound of Example 1. The product was triturated with ethyl ether/hexanes to provide the title compound, as a colorless solid; mp 155°–158° C. $[\alpha]_D^{25} = +168.0°$ (c=0.44, $CHCl_3$). Anal. Calc. for $C_{27}H_{26}N_5ClSO_4 \cdot 0.31 H_2O$: C, 58.15; H, 4.81; N, 12.56; Cl, 6.36; S, 5.75. Found: C, 58.39; H, 4.65; N, 12.32; Cl, 5.91; S, 5.81.

EXAMPLE 41

(3S-trans)-N-(4-Chlorophenyl)-N'-cyano-N"-[3,4-dihydro-3-hydroxy-2,2-dimethyl-6-[(1,2,3,4-tetrahydro-2-isoquinolinyl)sulfonyl]-2H-1-benzopyran-4-yl]guanidine

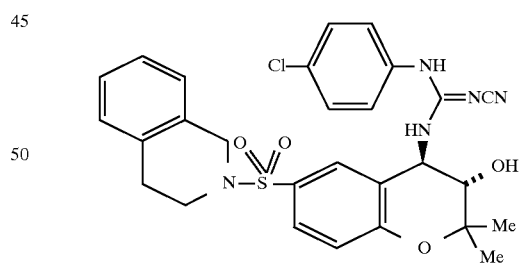

The title compound was prepared by the same procedure as described for the title compound of Example 1. The product was triturated with ethyl ether and hexanes to provide the title compound, as a colorless solid; mp 182°–185° C. (foaming, started @ 160° C.). $[\alpha]_D^{25} = +212.3°$ (c=0.483, $CHCl_3$). Anal. Calc. for $C_{28}H_{28}N_5ClSO_4$: C, 59.41; H, 4.99; N, 12.37; Cl, 6.26; S, 5.66. Found: C, 59.34; H, 4.88; N, 11.93; Cl, 5.34; S, 5.52.

EXAMPLE 42

(3S-trans)-N-(4-Chlorophenyl)-N'-cyano-N"-[3,4-dihydro-3-hydroxy-2,2-dimethyl-6-[(octahydro-1-quinolinyl)-sulfonyl]-2H-1-benzopyran-4-yl] guanidine

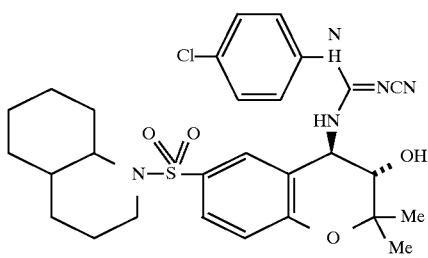

The title compound was prepared by the same procedure as described for the title compound of Example 1. The product was triturated with ethyl ether and hexanes to provide the title compound, as a colorless solid; mp 188°–190° C. (foaming, started @ 168° C.). $[\alpha]_D^{25}$ =+183.4° (c=0.325, CHCl$_3$). Anal. Calc. for $C_{28}H_{28}N_5ClSO_4$·0.12 $C_4H_{10}O$·0.2 $H_2O$: C, 58.51; H, 6.14; N, 11.98; Cl, 6.06; S, 5.48. Found: C, 58.52; H, 6.44; N, 11.56; Cl, 5.68; S, 5.17.

EXAMPLE 43

(3S-trans)-N-(4-Chlorophenyl)-N'-cyano-N"-[3,4-dihydro-3-hydroxy-2,2-dimethyl-6-(4-thiamorpholinylsulfonyl)-2H-1-benzopyran-4-yl] guanidine, 1,1-dioxide

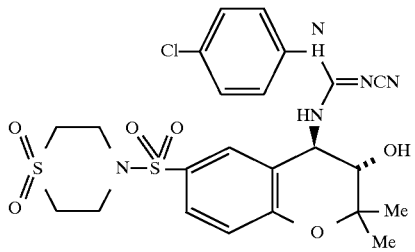

The title compound was prepared by the same procedure as described for the title compound of Example 1. The product was triturated with ethyl ether and hexanes to provide the title compound as a colorless solid; mp 185°–187° C. $[\alpha]_D^{25}$ =+157.6° (c=0.25, CHCl$_3$). Anal. Calc. for $C_{23}H_{26}N_5ClS_2O_6$·0.08 $C_4H_{10}O$·0.1 $H_2O$: C, 48.65; H, 4.73; N, 12.16; Cl, 6.16; S, 11.14. Found: C, 48.65; H, 4.58; N, 11.80; Cl, 6.30; S, 10.69.

EXAMPLE 44

(3R-trans)-1-[[4-[4-Chloro-N-(1H-imidazol-2-yl-methyl)-phenylamino]-3,4-dihydro-3-hydroxy-2,2-dimethyl-2H 1-benzopyran-6yl]sulfonyl]piperidine, monohydrochloride

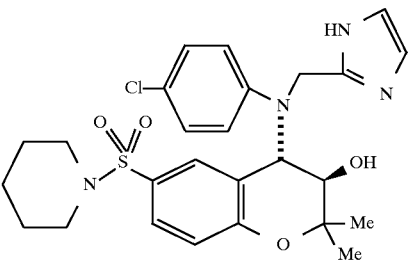

A. N-(4-Chlorophenyl)-N-[(1H-imidazol-2-yl)methyl]-amine

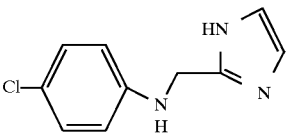

A mixture of 4-chloroaniline (66.65 g, 522.43 mmol) and 2-imidazolecarboxaldehyde (50.2 g, 522.43 mmol) in methanol (1000 mL) was stirred at 55°–60° C. overnight. The light brown reaction mixture was cooled in an ice bath and treated with sodium borohydride (21.74 g, 574.67 mrnol) in small portions. The reaction mixture was allowed to warm to room temperature and stirred for 2 hours. It was concentrated and partitioned between water (~500 nmL) and ethyl acetate (1200 mL), giving a white solid/aqueous layer and a brown organic layer. The organic layer was removed and the aqueous mixture was reextracted with ethyl acetate (3×200 mL). The combined organic layers were washed with brine, dried over sodium sulfate and concentrated. The resulting mixture was treated with hexanes and stored in the freezer for 2 hours. The white solid was collected by filtration and washed with cold ethyl acetate/hexane (2:1) to provide the title product (83.36 g, 77%) as a white solid, mp 163°–165° C. Anal. Calc. for $C_{10}H_{10}ClN_3$: C, 57.84; H, 4.85; N, 20.23; Cl, 17.07. Found: C, 57.82; H, 4.85; N, 20.04; Cl, 16.77.

B. (1aR-cis)-1-[(1a,7b-Dihydro-2,2-dimethyl-2H-oxireno[1]-[c]benzopyran-6-yl)sulfonyl]piperidine

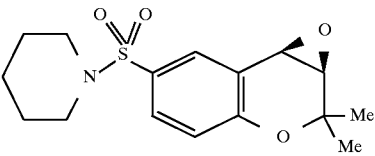

The title compound was prepared from the corresponding olefin (same procedure as described for the title E compound of Example 1) by the procedure of Lee et al, *Tetrahedron Letters*, 32, 5055 (1991), as described in the preparation of the title F compound of Example 1.

C. (3R-trans)-1-[[4-[4-Chloro-N-(1H-imidazol-2-yl-methyl)-phenylamino]-3,4-dihydro-3-hydroxy-2,2-dimethyl-2H-11-benzopyran-6-yl]sulfonyl]piperidine, monohydrochloride A solution of the title B compound (890 mg, 2.75 mmol) in acetonitrile (3 mL) was treated with the title A compound (572 mg, 2.75 mmol) and cobalt chloride (355 mg, 2.75 mmol). The reaction mixture was heated at 80° C. under argon for 2 hours and then at 60° C. for 18 hours. The blue-green solution was partitioned between ethyl acetate (100 mL) and water (100 mL) and the organic fraction was washed with brine (100 mL), dried (MgSO4), filtered through a plug of silica gel on celite and the solvent was removed to give a green oil. The residue was purified on silica gel using EtOAc/Hexane (40:60) to give a yellow oil. The oil was crystallized from dichloromethanehexanes to give a light yellow solid (340 mg, 23%) which in THF/MeOH (3:2, 4 mL) was converted to its hydrochloride salt by treatment with ethereal-HCl. The solvent was removed and the residue was triturated with hexanes to give a pale yellow solid (380 mg, 20%), mp 164° C. (softens at 170° C.). $[\alpha]_D$=+18.10° (c=0.37, MeOH). Anal. Calc. for $C_{26}H_{31}ClN_4O_4S.1.00$ HCl.1.08 H2O.0.17 Hexane: C, 53.94; H, 6.12; N, 9.31; Cl, 11.79; S, 5.33. Found: C, 53.95; H, 6.00; N, 8.87; Cl, 12.00; S, 4.91.

EXAMPLE 45

(3S-trans)-1-[[4-[4-Chloro-N-(1H-imidazol-2-yl-methyl)-phenylamino]-3,4-dihydro-3-hydroxy-2,2-dimethyl-2H-1-benzopyran-6-yl]sulfonyl]piperidine, monohydrochloride

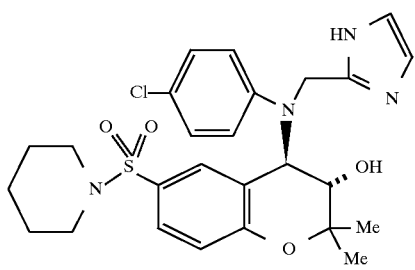

A. (1aS-cis)-1-[(1a,7b-Dihydro-2,2-dimethyl-2H-oxireno[1][c]benzopyran-6-yl)sulfonyl]piperidine

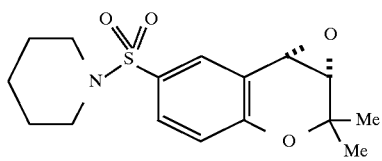

The title compound was prepared from the corresponding olefin (same procedure as described for title E compound of Example 1) by the procedure of Lee et al, *Tetrahedron Letters*, 32, 5055 (1991) as described in the preparation of the title F compound of Example 1.

B. (3S-trans)-1-[[4-[4-Chloro-N-(1H-imiidazol-2-yl-methyl)-phenylamino]-3,4-dihydro-3-hydroxy-2,2-dimethyl-2H-1-benzopyran-6-yl]sulfonyl]piperidine, monohydrochloride The title compound was prepared from the title A compound ((1aS-cis)-1-[(1a,7b-dihydro-2,2-dimethyl-2H-oxireno[1][c]benzopyran-6-yl)sulfonyl]piperidine) and title A compound of Example 44 (N-(4-chlorophenyl)-N-[(1H-imidazol-2-yl)methyl]amine) by the same procedure as described for the title compound of Example 44. mp 164° C. (softens at 170° C.). $[\alpha]_D$=−27.4° (c=0.5, MeOH). Anal. Calc. for $C_{26}H_{31}ClN_4O_4S.1.0$ HCl.0.63 H2O.0.16 THF: C, 54.50; H, 5.92; N, 9.54; Cl, 12.08; S, 5.46. Found: C, 54.43; H, 5.63; N, 9.17; Cl, 12.23; S, 5.86.

EXAMPLE 46

(3R-trans)-[N-[3,4-Dihydro-3-hydroxy-2,2-dimethyl-6-(1-piperidinylsulfonyl)-2H-1-benzopyran-4-yl]phenylamino]-acetic acid, ethyl ester

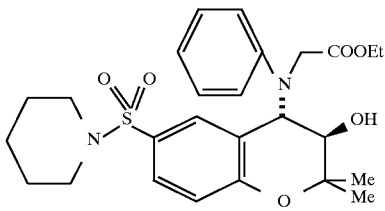

A solution of the title B compound of Example 44 (400 mg, 1.24 mmol) in $CH_3CN$ (500 μL) was treated with magnesium perchlorate (414 mg, 1.86 mmol) and N-phenylglycine ethyl ester (243 mg, 1.36 mmol). The solution was stirred at room temperature under argon for 18 hours, during which time the solution solidified. The reaction mixture was taken up in ethyl acetate (100 mL) and diluted with water (100 mL). The organic layer was separated and washed with $NaHCO_3$ solution, brine and dried over $MgSO_4$. The solvent was removed and the residue was purified by flash chromatography on silica gel using EtOAc:hexane (40:60) to give a white foam (340 mg, 80%), mp 95°–96.5° C. $[\alpha]_D$=+151.5° (c=0.40, MeOH). Anal. Calc. for $C_{26}H_{34}N_2O_6S.0.29$ $H_2O$: C, 61.49; H, 6.86; N, 5.52; S, 6.31. Found: C, 61.57; H, 6.82; N, 5.44; S, 6.40.

EXAMPLE 47

(3S-trans)-4-[(4-Chlorophenyl)(1H-imidazol-2-ylmethyl)-amino]-3,4-dihydro-3-hydroxy-2,2-dimethyl-N,N-bis(2-methylpropyl)-2H-1-benzopyran-6-sulfonamide

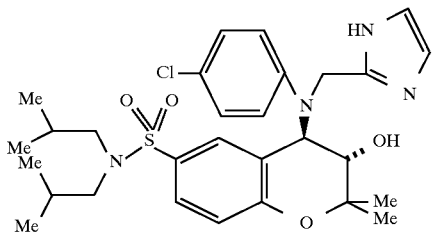

A. (1aS-cis)-1-[(1a,7b-dihydro-2,2-dimethyl-2,2-dimethyl-2H-oxireno[1][-[c]benzopyran-6-yl)-N,N-bis(2-methylpropyl)sulfonamide

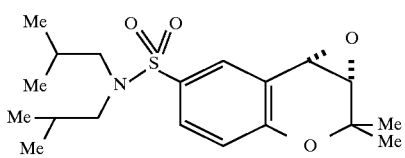

The title compound was prepared from the corresponding olefin (same procedure as described for the title E compound of Example 1) by the procedure of Lee et al, *Tetrahedron Letters*, 32, 5055 (1991), as described in the preparation of the title F compound of Example 1.

B. (3S-trans)-4-[(4-Chlorophenyl)(1H-imidazol-2-ylmethyl)-amino]-3,4-dihydro-3-hydroxy-2,2-dimethyl-N,N-bis (2-methylpropyl) -2H-1-benzopyran-6-sulfonamide.

A solution of the N-(4-chlorophenyl)-N-[(1H-imidazol-2-yl)methyl]amine (445 mg, 2.14 inmol, the title A compound of Example 44) in dry THF (2.5 mL), was cooled to −78° C. and treated with 2.5M n-butyllithium in hexanes (1.7 ml, 4.28 mmol). The solution was allowed to warm to −25° C. and stirred for 0.5 hours then cooled back to −78° C. A solution of the title A compound (785 mg, 2.14 mmol) in THF was added via syringe. The solution was stirred overnight under argon while warming to r.t. The solution was partitioned between ethyl acetate and (sat,.aq.) $NaHCO_3$ solution. The organic fraction was washed with brine, dried over $MgSO_4$, filtered and solvent was removed in vacuo to give a brown gum. The residue was purified on silica gel using 40:60/ethy acetate:hexane to give the title compound as a white solid (254 mg, 21%), mp 214°–216° C. (discoloration @ 185° C.). $[\alpha]_D$=−37.5°, (c=0.64, MeOH). Analysis calculated for $C_{29}H_{39}ClN_4O_4S$: C, 60.56, H, 6.83, N, 9.74, Cl, 6.16, S, 5.57. Found: C, 60.46, H, 6.93, N, 9.51, Cl, 5.87, S, 5.55.

Using the procedures described herein or by modification of the procedures described herein as known by one having ordinary skill in the art, the following additional compounds were also prepared.

| Example | Structure | M.P. 0° C. (solvent) | Rotation ($\alpha_D°$) | Analysis |
|---|---|---|---|---|
| 48 | 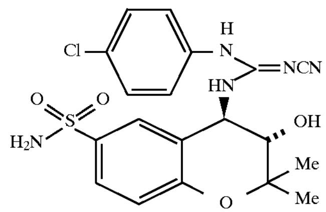 | 189 (foaming) | racemate | Calculated for $C_{19}H_{21}N_5O_4SCl\cdot0.34\ H_2O$: C, 50.04; H, 4.57; N, 15.35; Cl, 7.77; S, 7.03. Found: C, 50.33; H, 4.88; N, 15.06; Cl, 7.89; S, 6.66. |
| 49 | 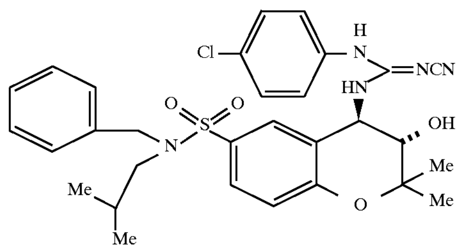 | 128–134 | +30.8 (c = 0.52, MeOH) | Calculated for $C_{30}H_{34}N_5O_4SCl\cdot0.83\ H_2O$: C, 60.44; H, 5.75; N, 11.75; Cl, 5.95; S, 5.38. Found: C, 59.10; H, 5.87; N, 11.49; Cl, 5.82; S, 5.26. |
| 50 | 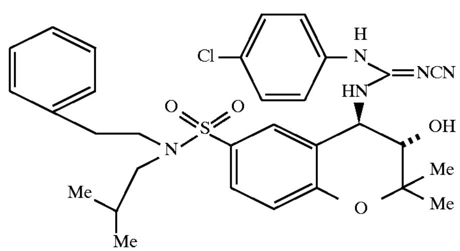 | 122–132 | +6.6 (c = 0.65, MeOH) | Calculated for $C_{23}H_{25}N_5O_4F_3SCl\cdot0.26\ H_2O$: C, 60.92; H, 6.10; N, 11.46; Cl, 5.80; S, 5.25. Found: C, 60.56; H, 5.99; N, 11.39; Cl, 5.77; S, 5.21. |
| 51 | 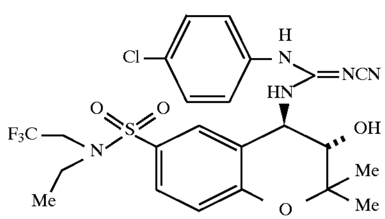 | 130–140 | +153 (c = 0.23, $CHCl_3$) | Calculated for $C_{23}H_{25}N_5O_4F_3SCl\cdot0.03\ C_6H_{14}$: C, 49.50; H, 4.56; N, 12.45; Cl, 6.30; S, 5.70. Found: C, 49.89; H, 4.38; N, 12.12; Cl, 6.44; S, 5.52. |

-continued

| Example | Structure | M.P. 0° C. (solvent) | Rotation ($\alpha_D°$) | Analysis |
|---|---|---|---|---|
| 52 | 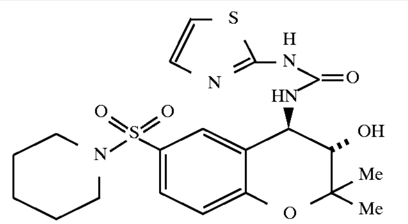 | 160–163 (softens @ 142) | −21.8 (c = 0.51, MeOH) | Calculated for $C_{20}H_{26}N_4O_5S_2 \cdot 0.3$ EtOAc: C, 51.65; H, 5.81; N, 11.36; S, 13.01. Found: C, 52.00; H, 6.03; N, 10.99; S, 12.71. |
| 53 | 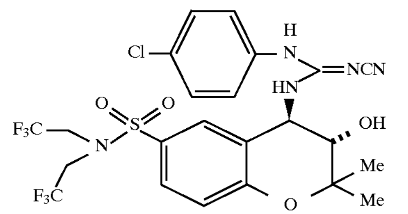 | 152–155 | +148.1 (c = 0.27, $CHCl_3$) | Calculated for $C_{23}H_{22}N_5O_4F_6SCl$: C, 45.0; H, 3.61; N, 11.41; Cl, 5.77; S, 5.22. Found: C, 45.24; H, 3.66; N, 11.53; Cl, 6.46; S, 4.78. |
| 54 | 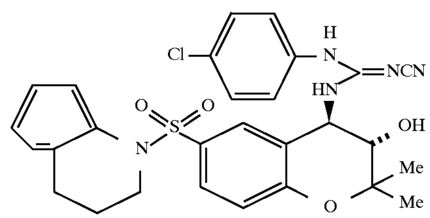 | 165–168 (foams) | +183.4 (c = 0.46, $CHCl_3$) | Calculated for $C_{28}H_{28}N_5O_4SCl \cdot 0.31$ $H_2O$: C, 58.82; H, 5.05; N, 12.25. Found: C, 59.13; H, 4.95; N, 11.94. |
| 55 | 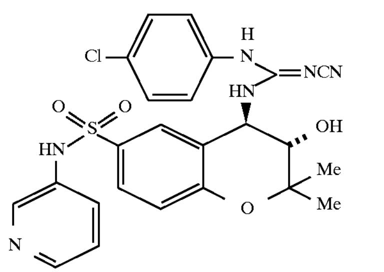 | 155 | | Calculated for $C_{24}H_{23}N_6O_4SCl \cdot 0.39$ $H_2O$: C, 53.98; H, 4.49; N, 15.74. Found: C, 53.98; H, 4.21; N, 14.75. |

| Example | Structure | M.P. 0° C. (solvent) | Rotation ($\alpha_D°$) | Analysis |
|---|---|---|---|---|
| 56 | 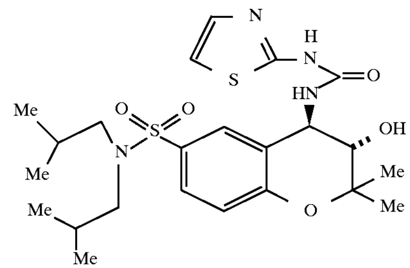 | 120–122 | | Calculated for $C_{23}H_{34}N_4O_5S_2 \cdot 0.5H_2O$: C, 53.15; H, 6.79; N, 10.78; S, 12.34. Found: C, 53.07; H, 6.97; N, 10.52; S, 12.02. |
| 57 | 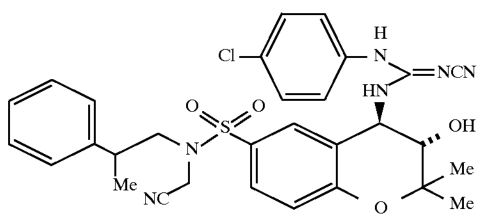 | 88–91 | +30.0 | Calculated for $C_{30}H_{31}N_6O_4SCl \cdot 1.30H_2O$: C, 57.15; H, 5.37; N, 13.33; Cl, 5.62; S, 5.08. Found: C, 57.13; H, 5.52; N, 13.52; Cl, 5.71; S, 4.95. |
| 58 | 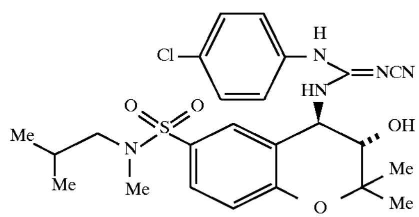 | 142–144 | −1.7 (c = 0.5, MeOH) | Calculated for $C_{24}H_{30}N_5O_4SCl \cdot 0.2H_2O \cdot 0.2CHCl_3$: C, 53.09; H, 5.63; N, 12.78; Cl, 10.36; S, 5.86. Found: C, 53.07; H, 5.58; N, 12.42; Cl, 10.17; S, 6.16. |
| 59 | 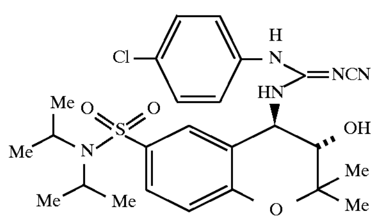 | 150 (softens) | | Calculated for $C_{25}H_{32}N_5O_4SCl$: C, 56.22; H, 6.04; N, 13.11; Cl, 6.64; S, 6.00. Found: C, 56.14; H, 6.04; N, 12.80; Cl, 6.93; S, 5.87. |

-continued

| Example | Structure | M.P. 0° C. (solvent) | Rotation ($\alpha_D°$) | Analysis |
|---|---|---|---|---|
| 60 | 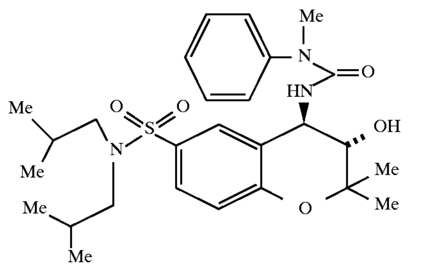 | 95–97 | +57.5 (c = 0.5, MeOH) | Calculated for $C_{27}H_{35}N_3O_5S \cdot 0.2H_2O$: C, 62.21; H, 7.62; N, 8.06; S, 6.15. Found: C, 62.01; H, 7.60; N, 7.86; S, 6.07. |
| 61 | 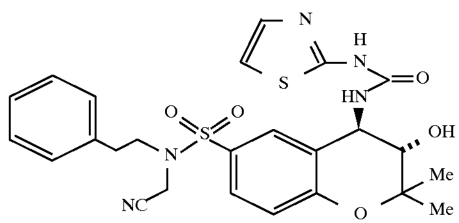 | 90 (softens) | −10.4 (c = 0.5, MeOH) | Calculated for $C_{25}H_{27}N_5O_5S_2$: C, 55.44; H, 5.02; N, 12.93; S, 11.84. Found: C, 55.11; H, 5.05; N, 12.98; S, 11.86. |
| 62 | 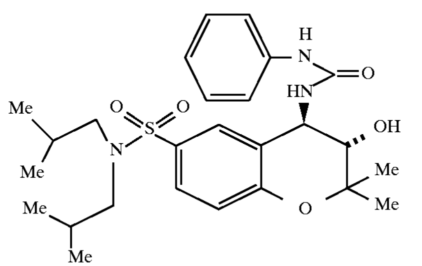 | 184–186 | | Calculated for $C_{26}H_{37}N_3O_5S$: C, 62.00; H, 7.40; N, 8.34; S, 6.37. Found: C, 62.35; H, 7.42; N, 8.33; S, 6.10. |
| 63 | 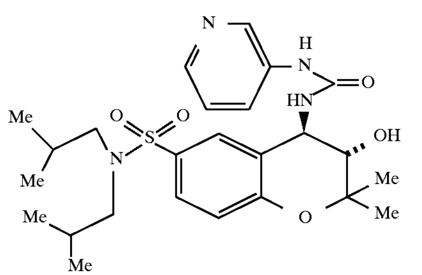 | 210–212 | | Calculated for $C_{25}H_{36}N_4O_5S$: C, 59.50; H, 7.19; N, 11.10; S, 6.35. Found: C, 59.28; H, 7.24; N, 10.93; S, 6.29. |

-continued

| Example | Structure | M.P. 0° C. (solvent) | Rotation ($\alpha_D°$) | Analysis |
|---|---|---|---|---|
| 64 | 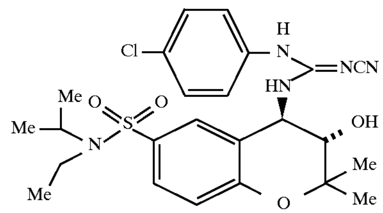 | 155–158 | −6.5 (c = 0.3, MeOH) | Calculated for $C_{24}H_{30}N_5O_4SCl\cdot0.50$ $H_2O\cdot0.25CHCl_3$: C, 52.11; H, 5.62; N, 12.53; Cl, 11.10; S, 5.74. Found: C, 52.03; H, 5.54; N, 12.42; Cl, 10.93; S, 5.74. |
| 65 | 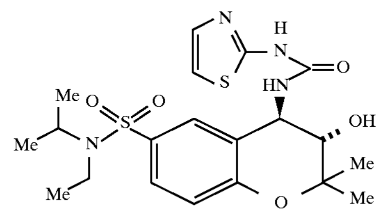 | 125–128 | −43 (c = 0.3, MeOH) | Calculated for $C_{20}H_{28}N_4O_5S_2\cdot0.50C_3H_7NO\cdot0.5CHCl_3$: C, 46.78; H, 5.71; N, 11.17; S, 11.35. Found: C, 47.11; H, 5.47; N, 10.90; Cl, 10.04. |
| 66 | 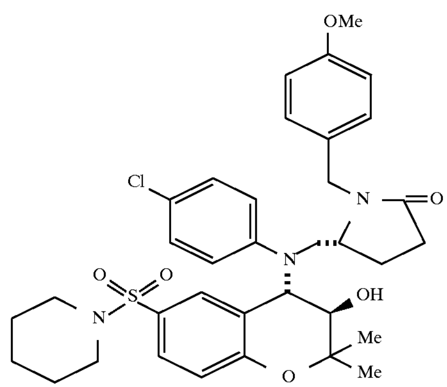 | 127–129 | −12.4 (c = 0.42, MeOH) | Calculated for $C_{35}H_{42}N_3O_6SCl\cdot0.63$ $H_2O$: C, 61.86; H, 6.42; N, 6.18; Cl, 5.22; S, 4.72. Found: C, 62.21; H, 6.42; N, 5.84; Cl, 5.35; S, 4.72. |
| 67 | 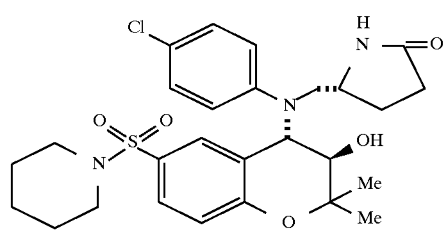 | >175 (decomposition) | +27.8 (c = 0.4, DMSO) | Calculated for $C_{27}H_{34}N_3O_5SCl\cdot1.1$ $H_2O\cdot0.1$ EtOAc: C, 57.49; H, 6.20; N, 6.87; Cl, 6.42. Found: C, 57.46; H, 6.20; N, 6.91; Cl, 6.42. |

-continued

| Example | Structure | M.P. 0° C. (solvent) | Rotation ($\alpha_D°$) | Analysis |
|---|---|---|---|---|
| 68 | 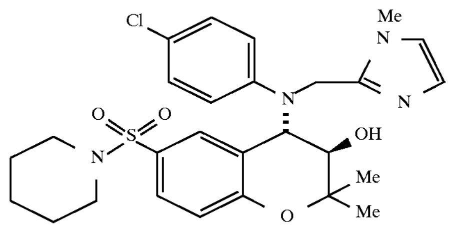 | 230–231 ((softens @ 195) | +7.2 (c = 0.33, MeOH) | Calculated for $C_{27}H_{33}N_4O_4SCl \cdot 0.7$ $H_2O \cdot 0.27EtOAc$: C, 59.49; H, 5.99; N, 10.15; Cl, 6.50; S, 5.88. Found: C, 59.09; H, 6.10; N, 10.28; Cl, 6.76; S, 5.66. |
| 69 | 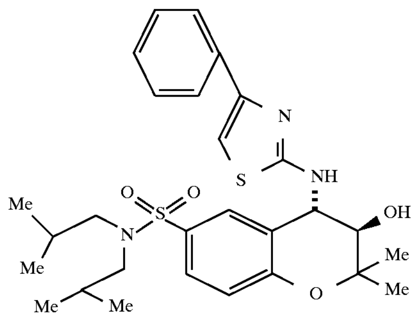 | 138–140 | +85.5 (c = 0.22, MeOH) | Calculated for $C_{28}H_{37}N_3O_4S_2$: C, 661.85; H, 6.86; N, 7.73; S, 11.79. Found: C, 62.08; H, 6.80 N, 7.55; S, 11.99. |
| 70 | 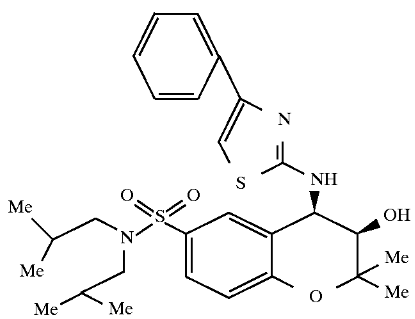 | 138–140 (softens 130) | −74.4 (c = 0.25, MeOH) | Calculated for $C_{28}H_{37}N_3O_4S_2$: C, 661.85; H, 6.86; N, 7.73; S, 11.79. Found: C, 61.83; H, 6.97; N, 7.46; S, 11.70. |

What is claimed is:

1. A compound of the formula

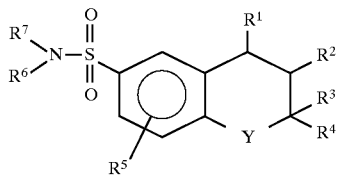

or a pharmaceutically acceptable salt thereof wherein $R^1$ is

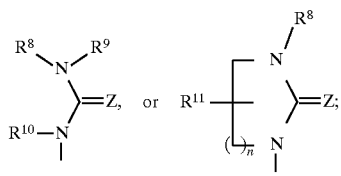

$R^2$ is hydrogen, hydroxy, or —OC(O)$R^{14}$;

$R^3$ and $R^4$ are each independently hydrogen, alkyl or arylalkyl; or $R^3$ and $R^4$ taken together with the carbon atom to which they are attached form a 3- to 7-membered carbocyclic ring;

$R^5$ is hydrogen, alkyl, halogen, heterocyclo, nitrile, haloalkyl or aryl;

$R^6$ and $R^7$ are independently hydrogen, alkyl, cycloalkyl, aryl, arylalkyl, haloalkyl, hydroxyalkyl, hydroxyalkyl substituted with a carboxylic ester or carboxylic acid, alkoxyalkyl, thioalkyl, (cycloalkyl)alkyl, morpholinylalkyl, heterocyclo or (heterocyclo) alkyl;

or $R^6$ and $R^7$ taken together with the nitrogen atom to which they are attached form a 5- to 7-membered mono or bicyclic ring including a fused ring which is 1-pyrrolidinyl, 1-piperidinyl, 1-azepinyl, 4-morpholinyl, 4-thiamorpholinyl, 4-thiamorpholine dioxide, 1-piperazinyl, 4-alkyl-1-piperazinyl, 4-arylalkyl-1-piperazinyl, 4-diarylalkyl-1-piperazinyl; or 1-piperazinyl, 1-pyrrolidinyl, 1-piperidinyl or 1-azepinyl substituted with one or more alkyl, alkoxy, alkylthio, halo, trifluoromethyl, hydroxy, aryl, arylalkyl, —COO$R^{14}$ or —CO—substituted amino;

or $R^5$ and $R^6$ taken together with the atoms to which they are attached form a 5- to 7-membered ring which contains two hetero atoms optionally substituted with aryl;

$R^8$ is aryl;

$R^9$ is hydrogen or alkyl;

$R^{10}$ and $R^{11}$ are independently hydrogen, alkyl, alkenyl, aryl, arylalkyl, cycloalkyl or cycloalkylalkyl; or $R^{11}$ can be an aryl group fused to 2 carbon atoms of the cyanoguanidine ring portion;

$R^{14}$ is hydrogen, alkyl, haloalkyl, aryl, arylalkyl, cycloalkyl or (cycloalkyl)alkyl;

Y is —O—;

Z is NCN;

n is an integer of 1 to 3.

2. The compounds as recited in claim 1 wherein Y is oxygen;

$R^1$ is

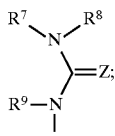

$R^2$ is hydroxyl;

$R^3$ and $R^4$ are methyl;

$R^6$ and $R^7$ are ethyl; or $R^6$ and $R^7$ taken together with the nitrogen atom to which they are attached form a 6-membered ring;

$R^8$ is phenyl;

$R^9$ is hydrogen; and $R^{10}$ is hydrogen.

3. The compounds as recited in claim 1 wherein Y is oxygen;

$R^1$ is

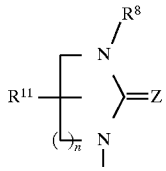

$R^2$ is hydroxyl;

$R^3$ and $R^4$ are methyl;

$R^6$ and $R^7$ are ethyl; or $R^6$ and $R^7$ taken together with the nitrogen atom to which they are attached form a 6-membered ring; and $R^{11}$ is hydrogen.

4. A compound as recited in claim 1, which is:

(3S-trans)-N-(4-chlorophenyl)-N'-cyano-N"-[6-[(diethylamino) sulfonyl]-3,4-dihydro-3-hydroxy-2,2-dimethyl-2H-1-benzopyran-4-yl]guanidine;

(3S-trans )-N-(4-chlorophenyl)-N'-cyano-N"-[3,4-dihydro-3-hydroxy-2,2-dimethyl-6-(1-piperidinylsulfonyl) -2H-1-benzopyran-4-yl] guanidine;

(3S-trans)-N-(4-chlorophenyl)-N'-cyano-N"-[3,4-dihydro-3-hydroxy-2,2-dimethyl-6-[(4-morpholinyl) sulfonyl]-2H-1-benzopyran-4-yl]guanidine;

(3S-trans,)-N-(4-chlorophenyl)-N"-cyano-N'-[3,4-dihydro-3-hydroxy-2,2-dimethyl-6-[[(phenylmethyl) amino]sulfonyl]-2H-1-benzopyran-4-yl]guanidine;

(3S-trans,)-N-(4-chlorophenyl)-N'-cyano-N"-[6-[(cyclohexylamino)sulfonyl]-3,4-dihydro-3-hydroxy-2, 2-dimeth-yl-2H-1-benzopyran-4-yl]guanidine;

(3S-trans)-1-[[4-[[[(4-chlorophenyl)amino](cyanoimino)-methyl]amino]-3,4-dihydro-3-hydroxy-1-2H-benzopyran-6-yl]sulfonyl]-2-piperidinecarboxylic acid, ethyl ester;

(3S-trans)-N-(4-chlorophenyl)-N'-cyano-N"-[3,4-dihydro-3-hydroxy-2,2-dimethyl-6-[(phenylamino) sulfonyl]-2H-1-benzopyran-4-yl]guanidine;

(3S-trans)-N-(4-chlorophenyl)-N'-cyano-N"-[3,4-dihydro-3-hydroxy-2,2-dimethyl-6-[[2-(phenylmethyl) -1-piperidinyl]-sulfonyl]-2H-1-benzopyran-4-yl] guanidine;

(3S-trans)-N-(4-chlorophenyl)-N'-cyano-N"-[3,4-dihydro-3-hydroxy-2,2-dimethyl-6-[(2-phenyl-1-piperidinyl)sulfonyl]-2H-1-benzopyran-4-yl]guanidine;

(3S-trans)-N-(4-chlorophenyl)-N'-cyano-N"-[3,4-dihydro-3-hydroxy-2,2-dimethyl-6-[[4-(phenylmethyl)-1-piperidinyl]-sulfonyl]-2H-1-benzopyran-4-yl]guanidine;

(3S-trans)-1-[[4-[[[(4-chlorophenyl)amino](cyanoimino)-methyl]amino]-3,4-dihydro-3-hydroxy-2,2-dimethyl-2H-1-benzopyran-6-yl]sulfonyl]-N-ethyl-2-piperidine-carboxamide;

(3S-trans)-[N-[[4-[[[(4-chlorophenyl)amino](cyanoimino)-methyl]amino]-3,4-dihydro-3-hydroxy-2,2-dimethyl-2H-1-benzopyran-6-yl]sulfonyl]phenylamino]acetic acid, ethyl ester;

(3S-trans)-N-(3-chlorophenyl)-N'-[6-[(diethylamino)-sulfonyl]-3,4-dihydro-3-hydroxy-2,2-dimethyl-2H-1-benzopyran-4-yl]urea;

(3S-trans)-N-(4-chlorophenyl)-N'-cyano-N"-[6-[(2-ethyl-1-piperidinyl)sulfonyl]-3,4-dihydro-3-hydroxy-2,2-dimethyl-2H-1-benzopyran-4-yl]guanidine;

(7S-trans)-N-(4-chlorophenyl)-N'-cyano-N"-(3,6,7,8-tetrahydro-7-hydroxy-6,6-dimethyl-2-phenyl-2H-pyrano-[2,3-f]-benzisothiazol-8-yl)guanidine, 1,1-dioxide;

trans-N-(4-chlorophenyl)-N'-cyano-N"-N-[3,4-dihydro-3-hydroxy-2,2-dimethyl-6-[(3-pyridinylamino)sulfonyl]-2H-1-benzopyran-4-yl]guanidine;

(3S-trans;)-N-(4-chlorophenyl)-N'-cyano-N"-N-[3,4-dihydro-3-hydroxy-2,2-dimethyl-6-[[(2-phenylethyl)(3-pyridinyl-methyl)amino]sulfonyl]-2H-1-benzopyran-4-yl]guanidine;

(3S-trans)-N-(4-chlorophenyl)-N'-cyano-N"-N-[6-[[(2,2-dimethylpropyl) (2phenylethyl) amino]sulfonyl]-3,4-dihydro-3-hydroxy-2,2-dimethyl-2H-1-benzopyran-4-yl]guanidine;

(3S-trans)-N-(4-chlorophenyl)-N'-cyano-N"-[6-[[ethyl (2-phenylethyl)amino]sulfonyl]-3,4-dihydro-3-hydroxy-2,2-dimethyl-2H-1-benzopyran-4-yl]guanidine;

(3S-trans)-N-(4-chlorophenyl)-N'-cyano-N"-[3,4-dihydro-3-hydroxy-2,2-dimethyl-6-[(3-methyl-1-piperidinyl)sulfonyl]-2H-1-benzopyran-4-yl]guanidine;

(3S-trans)-N-(4-chlorophenyl)-N'-cyano-N"-[3,4-dihydro-3-hydroxy-2,2-dimethyl-6-[(3,3-dimethyl-1-piperidinyl)-sulfonyl]-2H-1-benzopyran-4-yl]guanidine;

(3S-trans)-N-(4-chlorophenyl)-N'-cyano-N"-[3,4-dihydro-3-hydroxy-2,2-dimethyl-6-(1-pyrrolidinylsulfonyl)-2H-1-benzopyran-4-yl]guanidine;

(3S-trans)-N-(4-chlorophenyl)-N'-cyano-N"-[6-[(hexahydro-1H-azepin-1-yl)sulfonyl]-3,4-dihydro-3-hydroxy-2,2-dimethyl-2H-1-benzopyran-4-yl]guanidine;

(3S-trans)-N-(4-chlorophenyl)-N'-cyano-N"-[6-[(ethylphenylamino)sulfonyl]-3,4-dihydro-3-hydroxy-2,2-dimethyl-2H-1-benzopyran-4-yl]guanidine;

(3S-trans)-1-[[4-[[[(4-chlorophenyl)amino](cyanoimino)-methyl]amino]-3,4-dihydro-3-hydroxy-1-2H-benzopyran-6-yl]sulfonyl]-3-piperidinecarboxylic acid, ethyl ester;

(3S-trans)-4-[[4-[[[(4-chlorophenyl)amino](cyanoimino)-methyl]amino]-3,4-dihydro-3-hydroxy-1-2H-benzopyran-6-yl]sulfonyl]-1-piperazinecarboxylic acid, 1,1-dimethylethyl ester;

(3S-trans)-N-(4-chlorophenyl)-N'-cyano-N"-[3,4-dihydro-3-hydroxy-2,2-dimethyl-6-[(4-methyl-1-piperidinyl)sulfonyl]-2H-1-benzopyran-4-yl]guanidine;

(3S-trans)-N-(4-chlorophenyl)-N'-cyano-N"-[6-[[(cyanomethyl)(2-phenylethyl)amino]sulfonyl]-3,4-dihydro-3-hydroxy-2,2-dimethyl-2H-1-benzopyran-4-yl]guanidine;

(3S-trans)-N-(4-chlorophenyl)-N'-cyano-N"-[6-[[(cyanomethyl)(phenylmethyl)amino]sulfonyl]-3,4-dihydro-3-hydroxy-2,2-dimethyl-2H-1-benzopyran-4-yl]guanidine;

(3S-trans)-N-[6-[[bis(phenylmethyl)amino]sulfonyl]-3,4-dihydro-3-hydroxy-2,2-dimethyl-2H-1-benzopyran-4-yl]-N'-(4-chlorophenyl)-N"-cyanoguanidine;

[3S-[3a,4b,6(cis)]]-N-(4-chlorophenyl)-N'-cyano-N"-[6-[(2,6-dimethyl-1-piperidinyl)sulfonyl]-3,4-dihydro-3-hydroxy-2,2-dimethyl-2H-1-benzopyran-4-yl]guanidine;

(3S-trans)-N-[6-[[bis(2-methylpropyl)amino]sulfonyl]-3,4-dihydro-3-hydroxy-2,2-dimethyl-2H-1-benzopyran-4-yl]-N'-(4-chlorophenyl)-N"-cyanoguanidine;

(3S-trans)-N-(4-chlorophenyl)-N'-cyano-N"-[6-[[(cyanomethyl)(3-phenylpropyl)amino]sulfonyl]-3,4-dihydro-3-hydroxy-2,2-dimethyl-2H-1-benzopyran-4-yl]guanidine;

N-(4-chlorophenyl)-N'-cyano-N"-[(3S,4R)-6-[(3,5-dimethyl-1-piperidinyl)sulfonyl]-3,4-dihydro-3-hydroxy-2,2-dimethyl-2H-1-benzopyran-4-yl]guanidine;

N-(4-chlorophenyl)-N'-cyano-N"-[(3S,4R)-3,4-dihydro-3-hydroxy-2,2-dimethyl-6-[[3-(phenylmethyl)-1-piperidinyl]-sulfonyl]-2H-1-benzopyran-4-yl]guanidine;

(3S-trans)-N-[6-[(3-azabicyclo[3.2.2]nonan-3-yl)sulfonyl]-3,4-dihydro-3-hydroxy-2,2-dimethyl-2H-1-benzopyran-4-yl]-N'-(4-chlorophenyl)-N"-cyanoguanidine;

(3S-trans)-N-(4-chlorophenyl)-N'-cyano-N"-[3,4-dihydro-3-hydroxy-2,2-dimethyl-6-[(1,2,3,4-tetrahydro-1-quinolinyl)sufonyl]-2H-1-benzopyran-4-yl]guanidine;

(3S-trans)-N-(4-chlorophenyl)-N'-cyano-N"-[3,4-dihydro-3-hydroxy-2,2-dimethyl-6-[(1,2,3,4-tetrahydro-2-isoquinolinyl)sulfonyl]-2H-1-benzopyran-4-yl]guanidine;

(3S-trans)-N-(4-chlorophenyl)-N'-cyano-N"-[3,4-dihydro-3-hydroxy-2,2-dimethyl-6-[(1,2,3,4-tetrahydro-2-isoquinolinyl)sulfonyl]-2H-1-benzopyran-4-yl]guanidine;

(3S-trans)-N-(4-chlorophenyl)-N'-cyano-N"-[3,4-dihydro-3-hydroxy-2,2-dimethyl-6-[(octahydro-1-quinolinyl)sulfonyl]-2H-1-benzopyran-4-yl]guanidine.

5. A pharmaceutical composition comprising a compound of claim 1 and a pharmaceutically acceptable carrier.

6. A method for treating ischemia comprising administering to a mammalian specie in need thereof a therapeutically effective amount of a composition of claim 5.

* * * * *